US009157916B2

(12) United States Patent
Albitar et al.

(10) Patent No.: US 9,157,916 B2
(45) Date of Patent: *Oct. 13, 2015

(54) MEASURING CIRCULATING THERAPEUTIC ANTIBODY, ANTIGEN AND ANTIGEN/ANTIBODY COMPLEXES USING ELISA ASSAYS

(71) Applicant: Board of Regents, The University of Texas System, Austin, TX (US)

(72) Inventors: Maher Albitar, Sugar Land, TX (US); Michael J. Keating, Houston, TX (US); Taghi Manshouri, Houston, TX (US)

(73) Assignee: Board of Regents, The University of Texas Systems, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/305,430

(22) Filed: Jun. 16, 2014

(65) Prior Publication Data

US 2014/0335549 A1 Nov. 13, 2014

Related U.S. Application Data

(60) Division of application No. 13/934,940, filed on Jul. 3, 2013, now Pat. No. 8,790,882, which is a division of application No. 13/543,560, filed on Jul. 6, 2012, now Pat. No. 8,501,423, which is a division of application No. 13/349,170, filed on Jan. 12, 2012, now Pat. No. 8,232,068, which is a division of application No. 13/080,180, filed on Apr. 5, 2011, now Pat. No. 8,114,618, which is a continuation of application No. 12/761,903, filed on Apr. 16, 2010, now Pat. No. 7,943,332, which is a division of application No. 10/251,144, filed on Sep. 20, 2002, now Pat. No. 7,718,387.

(60) Provisional application No. 60/323,679, filed on Sep. 20, 2001.

(51) Int. Cl.
*G01N 33/53* (2006.01)
*G01N 31/00* (2006.01)
*G01N 33/574* (2006.01)
*G01N 33/564* (2006.01)
*G01N 33/68* (2006.01)

(52) U.S. Cl.
CPC ........ *G01N 33/57492* (2013.01); *G01N 33/564* (2013.01); *G01N 33/57407* (2013.01); *G01N 33/6893* (2013.01); *Y10S 424/81* (2013.01); *Y10S 436/809* (2013.01); *Y10T 436/106664* (2015.01); *Y10T 436/107497* (2015.01)

(58) Field of Classification Search
CPC ............ G01N 33/564; G01N 33/6893; G01N 33/57407; Y10S 424/81; Y10S 436/809
See application file for complete search history.

(56) References Cited

U.S. PATENT DOCUMENTS

| | | | |
|---|---|---|---|
| 4,376,110 A | 3/1983 | David et al. | 435/5 |
| 5,059,522 A | 10/1991 | Wayne | 435/7.2 |
| 5,227,159 A | 7/1993 | Miller | 424/131.1 |
| 5,234,816 A | 8/1993 | Terstappen | 435/7.24 |
| 5,426,029 A | 6/1995 | Rittershaus et al. | 435/7.21 |
| 5,525,461 A | 6/1996 | Rittershaus | 435/5 |
| 5,597,735 A | 1/1997 | Laszlo et al. | 436/525 |
| 5,667,981 A | 9/1997 | Groffen et al. | 435/7.23 |
| 5,700,649 A | 12/1997 | Morton et al. | 435/7.1 |
| 5,726,064 A | 3/1998 | Robinson et al. | 436/514 |
| 5,736,137 A | 4/1998 | Anderson et al. | 424/133.1 |
| 6,090,365 A | 7/2000 | Kaminski et al. | 424/1.49 |
| 7,718,387 B2 * | 5/2010 | Albitar et al. | 435/7.92 |
| 7,943,332 B2 * | 5/2011 | Albitar et al. | 435/7.21 |
| 8,114,618 B2 * | 2/2012 | Albitar et al. | 435/7.21 |
| 8,232,068 B2 * | 7/2012 | Albitar et al. | 435/7.21 |
| 8,501,423 B2 * | 8/2013 | Albitar et al. | 435/7.21 |
| 8,790,882 B2 * | 7/2014 | Albitar et al. | 435/7.21 |
| 2002/0019018 A1 | 2/2002 | Christopherson et al. | 435/7.23 |

FOREIGN PATENT DOCUMENTS

WO WO 00/39580 7/2000

OTHER PUBLICATIONS

Kossman et al. Clinical Cancer Research, vol. 5, pp. 2748-2755, Oct. 1999.*
"Diagnostic Tests, Evaluation of" In: Encyclopedia of Biostatistics, Armitage & Colton, Eds., John Wiley & Sons, Inc. vol. 2, pp. 1149-1155, 1998.
"Standard Error," In: Encyclopedia of Biostatistics, Armitage & Colton, Eds., John Wiley & Sons, vol. 6, p. 4232, Inc. , 1998.
Belov et al. "Immunophenotyping of leukemias using a cluster of differentiation antibody microarray" Cancer Res.; 61:4483-4489, 2001.
Binet, et al. "A clinical staging system for chronic lymphocytic leukemia" Cancer; 40:855-864, 1977.
Center for Drug Evaluation and Research, "Application No. NDA 21174, Clinical Pharmacology and Biopharmaceutics Review(s)," found at http://www.fda .gov/cder/foi/nda/2000/2 li 74_MYLOTARG_biopharmr. pdf, 2000.
Center for Drug Evaluation and Research, "Application No. 103948/0, Clinical pharmacology and Biopharmaceutics Review(s)," found at http:/lwww.fda.gov/cder/foi/nda/2000/1 03948_0000_Campath_ClinPharm.pdf, 2001.
Center for Drug Evaluation and Research, "Clinical Review of BLA Reference No. BLA 97-0260 and BLA 97-0244," found at http://www.fda.gov/cder/biologicslr-eview/ritugenl 12697-rl.pdf, 1997.

(Continued)

Primary Examiner — Lisa Cook
(74) Attorney, Agent, or Firm — Parker Highlander PLLC

(57) ABSTRACT

The present invention relates to the field of immunology and hyperproliferative diseases. More specifically, the present invention relates to a method of detecting and monitoring therapeutic antibody:antigen complex, soluble antigen and soluble therapeutic antibody, wherein a patient has undergone at least one course of immunotherapy. Yet further, levels of therapeutic antibody:antigen complexes, soluble antigens or soluble therapeutic antibodies may be measured and used to stage or monitor a hyperproliferative disease.

6 Claims, 15 Drawing Sheets

(56) References Cited

OTHER PUBLICATIONS

Dillman, "Infusion reactions associated with the therapeutic use of monoclonal antibodies in the treatment of malignancy," *Cancer and Metastasis Reviews*, 18:465-71, 1999.

Durrant, I. & Fowler, S., Chemiluminescent detection systems for protein blotting,*In*: Protein Blotting: A Practical Approach, Chapter 11, pp. 141-152, Dunbar, B.S., Ed., Oxford University Press, Inc., 1994.

Dyer et al., "Effects of CAMPATH-1 antibodies in vivo in patients with lymphoid malignancies: influence of antibody isotype," *Blood*, 73:1431-1439, 1989.

Extended European Search Report, issued in European Application No. 09168283.1, mailed Jun. 4, 2010.

Ferrone, S. & Pellegrino, M.A. HL-A antigens, antibody, and complement in the lymphocytotoxic reaction, *In*: Contemporary Topics in Molecular Immunology, Reisfeld & Mandy, Eds., Plenum Press, vol. 2, pp. 185-235, 1973.

Foran et al., "European phase II study of Rituximab (chimeric anti-CD20 monoclonal antibody) for patients with newly diagnosed mantle-cell lymphoma and previously treated mantle-cell lymphomas, immunocytoma, and small B-cell lymphocytic lymphoma," *J. Clin. Oncol.*, 18:317-24, 2000.

Ginaldi, L. et al. Levels of expression of CD52 in normal and leukemic B and T cells: correlation with in vivo therapeutic responses to CAMPATH-1H *Leuk Res.*;22:185-191, 1998.

Green et al., "Application No. 103948/0—Clinical Pharmacology and Biopharmaceutics Review(s)," retrieved from http://www.accessdata.fda.gov/drugsatfda_docs/nda/2000/103948_0000_Campath_ClinPharm.pdf, retrieved on Apr. 20, 2010.

Green et al., "Application No. 103948/0—Pharmacology Review," retrieved from http://www.accessdata.fda.gov/drugsatfda_docs/nda/2000/103948_0000_Campath_PharmTox.pdf, retrieved on Apr. 20, 2010.

Haisma et al., "Antibody-antigen complex formation following injection of OC125 monoclonal antibody in patients with ovarian cancer," *Int. J Cancer*, 40:758-62, 1987.

Heegaard & Bjerrum, Immunoblotting—General Principles and Procedures, *In*: CRC Handbook of Immunoblotting of Proteins, Bjerrum & Heegaard, Eds., CRC Press Inc., vol. 1, Section 1, pp. 1-25, 1988.

Herold, M. et al. Successful treatment and re-treatment of resistant B-cell chronic lymphocytic leukemia with the monoclonal anti-CD 20 antibody rituximab *Ann. Hematol.*, 2000;79:332-335.

Maheu, M. et al. Immunologic diagnosis and monitoring of human acute leukemias. *Cancer*, 40:855-64, 1977.

Manshouri et al., "Clinical Relevance of Circulating CD20 (cCD20) in Patients with Chronic Lymphocytic Leukemia (CLL)," *Blood*, 96(11): 369a, 2000 [abstract].

Manshouri et al., "Soluble CD52 is detectable in the plasma of patients with chronic lymphocyte leukemia," *Blood*, 98:149a, 2001.

McLaughlin et al., "Rituximab chimeric anti-CD20 monoclonal antibody therapy for relapsed indolent lymphoma: half of patients respond to a four-dose treatment program," *J Clin. Oncol.*, 16:2825-33, 1998.

Milennium and ILEX Partners, LP: Campath 10-14 (Alemtuzumab), May 2, 2001, retrieved from http://www.fda.gov/downloads/Drugs/DevelopmentApprovalProcess/HowDrugsareDevelopedandApproved/ApprovalApplications/TherapeuticBiologicApplications/ucm088606.pdf, retrieved on Apr. 20, 2010.

Muniz, M. et al., "Protein sorting upon exit from the endoplasmic reticulum" *Cell*, 2001;104:313-320.

Nguyen et al., "IDEC-C2B8 anti-CD20 (Rituximab) immunotherapy in patients with low-grade non-Hodgkin's lymphoma and lymphoproliferative disorders: evaluation of response on 48 patients," *Eur. J Haematol.*, 62:76-82, 1999.

Office Action issued in Japanese Application No. 2003-528839, mailed Aug. 4, 2009.

Office Action issued in Japanese Application No. 2003-528839, mailed Sep. 16, 2008.

Office Action issued in Japanese Application No. 2009-008263 (and English language partial translation thereof), mailed Jan. 27, 2012.

Office Action issued in U.S. Appl. No. 10/251,144, dated Feb. 23, 2006.

Office Action issued in U.S. Appl. No. 10/251,144, dated Jul. 22, 2005.

Office Action issued in U.S. Appl. No. 10/251,144, dated Mar. 8, 2007.

Office Action issued in U.S. Appl. No. 10/251,144, dated Mar. 12, 2009.

Office Action issued in U.S. Appl. No. 10/251,144, dated Nov. 16, 2005.

Office Action issued in U.S. Appl. No. 13/080,180, mailed Sep. 12, 2011.

Office Action issued in U.S. Appl. No. 13/543,560, mailed Dec. 6, 2012.

Office Action issued in U.S. Appl. No. 13/934,940, mailed Nov. 15, 2013.

PCT International Preliminary Examination Report issued in International Application No. PCT/US2002/030142, completed Dec. 2, 2004.

PCT International Search Report issued in International Application No. PCT/US2002/030142, mailed May 22, 2003.

Polliach et al., "Myelomonocytic Antigens are Rarely Expressed on B-Lymphocytic Leukemia Cells," *Leukemia and Lymphoma*, 9: 125-131, 1993.

Rai, K.R. et al. "Clinical staging of chronic lymphocytic leukemia" *Blood*, 1975;46:219-234.

Random House Webster's Unabridge Dictionary, $2^{nd}$ Edition, New York, pp. 1242, 1998.

Reference Base, *In*: NIST/Sematech e-Handbook of Statistical Methods, Section 2.1.1.2, Croarkin, C. & Tobias, P., Eds., available at <http://www.itl.nist.gov/div898/handbook/>, retrieved Apr. 22, 2008.

Rowan et al., "Cross-linking of the CAMPATH-1 antigen (CD52) mediates growth inhibition in human B- and T-lymphoma cell lines, and subsequent emergence of CD52-deficient cells," *Immunology*, 95:427-436, 1998.

Sakahara et al., "Effect of circulating antigen on immunoscintigraphy of ovarian cancer patients using anti-CA125 monoclonal antibody," *Japan J. Cancer Res.*, 87:655-61, 1996.

Schrohenloher et al., "Circulating Antibody—Antigen complexes in human disease: possible occurrence in cancer," *Ala. J Med. Sci.*, 14:10-20, 1977.

Sievers, "Clinical studies of new "biologic" approaches to therapy of acute myeloid leukemia with monoclonal antibodies and immunoconjugates," *Curr. Opin. Oncol.*, 12:30-5, 2000.

Weiner, "An overview of monoclonal antibody therapy of cancer," *Semin. Oncol.*, 26:41-50, 1999.

\* cited by examiner

MEASURING CIRCULATING THERAPEUTIC ANTIBODY, ANTIGEN AND ANTIGEN/ANTIBODY COMPLEXES USING ELISA ASSAYS

This application is a divisional of U.S. patent application Ser. No. 13/934,940, filed Jul. 3, 2013, now U.S. Pat. No. 8,790,882, which is a divisional of U.S. patent application Ser. No. 13/543,560, filed Jul. 6, 2012, now U.S. Pat. No. 8,501,423, which is a divisional of U.S. patent application Ser. No. 13/349,170, filed Jan. 12, 2012, now U.S. Pat. No. 8,232,068, which is a divisional of U.S. patent application Ser. No. 13/080,180, filed Apr. 5, 2011, now U.S. Pat. No. 8,114,618, which is a continuation of U.S. patent application Ser. No. 12/761,903, filed Apr. 16, 2010, now U.S. Pat. No. 7,943,332, which is a divisional of U.S. application Ser. No. 10/251,144, filed on Sep. 20, 2002, now U.S. Pat. No. 7,718,387, which claims priority to U.S. Provisional Application No. 60/323,679, filed Sep. 20, 2001. The entire text of each of the above referenced disclosures is specifically incorporated herein by reference.

BACKGROUND OF THE INVENTION

A. Field of Invention

The present invention relates to the field of immunology and hyperproliferative diseases. More particularly, the present invention relates to a method of detecting and monitoring a therapeutic antibody:antigen complex, soluble antigen, free therapeutic antibody and soluble total therapeutic antibody, wherein a patient has undergone at least one dose of immunotherapy. Yet further, the methods may be used to monitor or stage a hyperproliferative disease by measuring the levels of therapeutic antibody:antigen complexes, soluble antigens or soluble therapeutic antibodies.

B. Description of the Related Art

1. Clusters of Differentiation

Clusters of differentiation (CD) have been established to define human leukocyte differentiation antigens (Bernanrd and Boumsell, 1984) by the comparison of reactivities of monoclonal antibodies directed against the differentiation antigens. These cell surface antigens serve as markers of cell lineage and distinguish populations of leukocytes with different functions, e.g., neutrophils and monocytes.

Leukocyte cell surface antigens have enormous clinical application potential for the identification of leukocyte populations and their functional status (Krensky, 1985, Kung et al., 1984; Kung et al., 1983; Cosimi et al., Knowles et al., 1983; and Hoffman, 1984). For example, measuring the total numbers of T cells by surface markers has been useful for the characterization, diagnosis and classification of lymphoid malignancies (Greaves, et al., 1981) and viral infection associated with transplantation (Colvin, R. B et al., 1981), and AIDS (Gupta, 1986; Ebert et al., 1985).

a) CD20

CD20, also called B1 (Bp35), is a cell surface phosphoprotein detected on the surface of B-lymphocytes (Tedder and Schlossman, 1988; Warzynski et al., 1994; Algino et al. 1996). CD20 has a major role in the regulation of human B-cell activation, proliferation and differentiation (Golay et al., 1985; Tedder and Engel, 1994; Kehrl et al., 1994). It has been reported that CD20 is heavily phosphorylated in malignant B-cells and proliferating B-cells when compared to non-proliferating B-cells (Tedder and Schlossman, 1988). Based on sequence analysis, the CD20 molecule appears to have four transmembrane domains with n- and c-terminal domains in the cytoplasm (Kehrl, et al., 1994). The molecule appears to regulate transmembrane $Ca^{++}$ conductance (Tedder and Engel, 1994). Antibodies directed towards the extracellular portion of CD20 appear to activate a tyrosine kinase pathway that modulates cell cycle progression by interaction with src-related kinases (Deans et al., 1995; Popoff et al. 1998; Hofmeister et al., 2000). Relocalization of CD20 into a detergent-insoluble membrane compartment upon binding to antibodies has also been reported (Deans et al., 1998). Several investigators have documented variations in the intensity of CD20 expression on the surface of malignant B-cells in different lymphoproliferative diseases (Almasri et al., 1992; Ginaldi et al., 1998). This is important in view of the success an anti-CD20 monoclonal antibody (Rituximab) in treating various B-cell malignancies (Maloney et al., 1999; Dimopoulous et al., 2000; Zinzani et al., 2000; Hainsworth, 2000; Keating et al., 2000; McLaughlin et al., 2000: Kuehnle et al., 2000). The reported structure of the CD20 molecule suggests that it is not secreted and is highly unlikely to be shed from the cell surface (Riley et al., 2000).

b) CD52

The CD52 antigen is a glycoprotein with a very short mature protein sequence consisting of 12 amino acids, but with a large carbohydrates domain (approximately 3 times the size of the protein domain) (Xia, M. Q. et al., 1993; Treumann, A. et al., 1995). CD52 is expressed on the surface of T- and B-lymphocytes, monocyte/macrophages, eosinophils and some hematopoietic progenitors (Rowan, W. et al., 1998; Elsner, J. et al., 1996; Taylor, M. L. et al., 2000; Gilleece, M. H. et al., 1993). CD52 is also expressed in the male reproductive tract, mainly in the epithelial lining cells of the distal epidermis, vas deferens, and seminal vesicles (Kirchhoff, C. et al., 1995; Kirchhoff, C. et al., 1993; Kirchhoff, C. 1996; Kirchhoff, C. et al., 1997; Kirchhoff, C., 1998; Kirchhoff, C. et al., 2000). CD52 is necessary for spermatozoa to preserve normal motility. It is shed into seminal plasma and then acquired by sperm cells to enable their passage through the genital tract, thus it is detectable on the surface of epididymal sperm and in the ejaculate, but not on either spermatogenetic cells or testicular spermatozoa. The protein core of the sperm and lymphocyte CD52 is identical—both are products of a single copy gene located on chromosome 1(1p36) (Tone, M. et al., 1999). However, N-linked carbohydrate side chains and the GPI-anchor structure are different. The physiological role of CD52 on lymphocytes is unclear.

The Campath-1 family of monoclonal antibodies was originally generated by immunizing rats against human T-cells (Friend, P. J. et al., 1991). Later studies show that Campath-1 antibodies recognize CD52 (Xia, M. Q. et al., 1993; Xia, M. Q. et al., 1991; Hale, G. et al., 1990). Several forms, both IgG and IgM, were generated. The IgG1 form of Campath-1 was humanized and this agent, Campath-1H (Alemtuzumab), has recently been approved for the treatment of refractory chronic lymphocytic leukemia (CLL) Finkelstein, J. B. et al., 2001; Rawstron, A. C. et al., 2001; Riechmann, L. et al., 1988). The Campath-1 family of antibodies is also being used in vitro for lymphocyte depletion in allogeneic marrow grafts and is being investigated as immunomodulatory therapy in a variety of diseases (Moreau, T. et al., 1996; Matteson, E. L. et al., 1995; Lim, S. H. et al., 1993; Lockwood, C. M. et al., 1993; Lockwood, C. M., 1993; Lockwood, C. M. et al., 1996; Dick, A. D. et al., 2000; Hale, G. et al., 2000; Isaacs, J. D. et al., 1992; Lim, S. H. et al., 1993; Mehta, J. et al., 1997; Naparstek, E. et al., 1999; Naparstek, E. et al., 1995; Novitzky, N. et al., 1999; Or, R. et al., 1994).

Antibodies against CD52 are believed to initiate killing of cells through antigen cross-linking (Hale, C. et al., 1996). As a result of this cross-linkage, several cytokines are released including tumor necrosis factor-α, interferon γ and interleukin (Elsner, J. et al., 1996; Wing, M. G. et al., 1996; Wing, M. G. et al., 1995). Cross-linking of CD52 by antibodies promotes apoptosis and antibody-dependent cellular cytotoxicity, which may count for the effectiveness of Campath-1H in treating patients with chronic lymphocytic leukemia (CLL) (Rowan, W. et al., 1998; Rawstron, A. C. et al., 2001; Greenwood, J. et al., 1994; Xia, M. Q., et al., 1993). CD52 is expressed on the surface of neoplastic lymphocytes in patients with CLL, low-grade lymphomas and T-cell malignancies (Dyer, M. J., 1999; Dybjer, A. et al., 2000; Pawson, R. et al., 1997; Salisbury, J. R. et al., 1994; Matutes, E. 1998). Some cases of myeloid, monocytic and acute lymphoblastic leukemia also express CD52 (Belov, L. et al., 2001; Hale, G. et al., 1985). This wide expression of CD52 in a variety of hematological malignancies has led to increasing interest in using Campath-1H in treating these malignancies (Khorana, A. et al., 2001; Keating, M. J. 1999).

CD52 is shed in the male productive system and the soluble molecules play an important role in preserving spermatozoa function (Kirchhoff, C., 1996; Yeung, C. H. et al., 1997; Yeung, C. H. et al., 2001). However, it is not known if CD52 is shed from hematopoietic cells and/or detectable in the circulation of patients with CLL.

c) CD33

CD33 is a member of the siglecs family which bind sialic acid. CD33 is restricted to the myelomonocytic lineage of cells. During maturation of myeloid cells, the pluripotent hematopoietic stem cells give rise to progenitor cells that have a diminished self-renewal capacity and a greater degree of differentiation. During this development, normal myeloid cells express cell surface antigens, for example CD33. CD33 is present on maturing normal hematopoietic cells, however, normal hematopoietic stem cells lack this cell surface antigen. In addition to maturing normal hematopoietic cells, CD33 is also present on acute myelocytic leukemia (AML). Thus, this myeloid cell surface maker has become an attractive target for monoclonal antibody targeting. Yet further, anti-CD33 antibodies have also been used to deliver radiation or a cytotoxic agent directly to leukemic cells.

2. Immunoassays

Immunoassays are usually used to measure cell surface antigens. Typically, immunofluorescence using flow cytometry is the immunoassay of choice. However, other immunoassays may be used, for example enzyme linked immunosorbant assays (ELISA). This technique is based upon the special properties of antigen-antibody interactions with simple phase separations to produce powerful assays for detecting biological molecules.

One well-known and highly specific ELISA is a sandwich ELISA. In this assay, the antibody is bound to the solid phase or support, which is then contacted with the sample being tested to extract the antigen from the sample by formation of a binary solid phase antibody:antigen complex. After a suitable incubation period, the solid support is washed to remove the residue of the fluid sample and then contacted with a solution containing a known quantity of labeled antibody.

The methodology and instrumentation for the ELISA is simpler than that for immunofluorescence. Yet further, the ELISA and immunofluorescence assays are completely different assays. ELISA assays measure the protein (antigen) in the plasma/serum, which reflects the entire body. Surface immunofluorescent assays measure an antigen on the surface of individual cells and does not provide information on the amount of cells in the body. Thus, there are advantages in developing an ELISA assay to provide a measurement of the entire body.

BRIEF SUMMARY OF THE INVENTION

It is, therefore, an objective of the present invention to provide methods for detecting or monitoring soluble leukocyte surface molecules, such as cell differentiation antigens or fragments thereof. Specifically, soluble surface antigen, antibody:antigen complexes and antibodies that are directed to cell differentiation antigens may be detected or monitored by using a modified sandwich ELISA technique. Also, soluble cell surface molecules as quantified using the modified sandwich ELISA technique can be used to monitor proliferation and cell volume in individuals with cancer or other hyperproliferation diseases due to any other process, such as inflammation or infection.

In specific embodiments, the antibody:antigen complex is measured in a patient that has undergone at least one course, e.g., an injection, of immunotherapy with a therapeutic antibody. The therapeutic antibody may include, but is not limited to anti-CD20, anti-CD52 or anti-CD33. The antibody:antigen complex is measured by ELISA techniques and provides a determination of the efficacy of the antibody immunotherapy.

Another aspect of the present invention includes a method of providing an immunotherapy to a patient comprising administering to the patient a therapeutic antibody and detecting the presence of a circulating antibody:antigen complex, total antibody, free antigen and free antibody. The therapeutic antibody binds to a soluble antigen, which is shed from the cell surface. It is envisioned that the antigen is CD20, CD52 and CD33. It is envisioned that these methods can be used to monitor the efficacy of antibody-based therapy.

In further embodiments, the present invention provides methods for detecting or monitoring hyperproliferative diseases by measuring soluble leukocyte surface molecules, therapeutic antibodies, or antibody:antigen complexes. Specifically, a sample from a patient is obtained, the sample is contacted with a first monoclonal antibody, in which the antibody captures the complex; the complex is contacted with a labeled second antibody; and the labeled complex is measured. The first monoclonal antibody is bound to a solid surface. Yet further, the patient has undergone a course of immunotherapy with a therapeutic antibody in which the therapeutic antibody binds to a soluble circulating target antigen forming the complex.

Hyperproliferative disease as used herein may be further defined as cancer. Yet further, cancer is further defined as a neoplasm. Exemplary neoplasms include, but are not limited to melanoma, non-small cell lung, small-cell lung, lung hepatocarcinoma, retinoblastoma, astrocytoma, gliobastoma, gum, tongue, leukemia, neuroblastoma, head, neck, breast, pancreatic, prostate, renal, bone, testicular, ovarian, mesothelioma, cervical, gastrointestinal, lymphoma, brain, colon, or bladder.

It is also contemplated that hyperproliferative disease may be further defined as an autoimmune disease, for example, but not limited to Sjögren's syndrome, rheumatoid arthritis, systemic lupus erythematosus, autoimmune thyroid disease, refractory ocular inflammatory disease, multiple sclerosis, Wegener's granulomatosis or infection.

In specific embodiments, the present invention monitors, detects or stages a hematopoietic neoplasm. Exemplary hematopoietic neoplasms, include, but are not limited to chronic lymphocytic leukemia, acute myelogenous leukemia, acute lymphoblastic leukemia, myelodysplastic syndrome, chronic myelomonocytic leukemia, juvenile myelomonocyte leukemia, multiple myeloma, lymphoma, T-cell chronic lymphocytic leukemia or prolymphocytic leukemia.

Yet further, it is contemplated that the present invention may be used to determine tumor mass. Tumor mass may be determined using the modified sandwich ELISA of the present invention to measure the levels of soluble leukocyte cell surface antigens, soluble antibodies or soluble antibody:antigen complexes.

The use of the word "a" or "an" when used in conjunction with the term "comprising" in the claims and/or the specification may mean "one," but it is also consistent with the meaning of "one or more," "at least one," and "one or more than one."

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
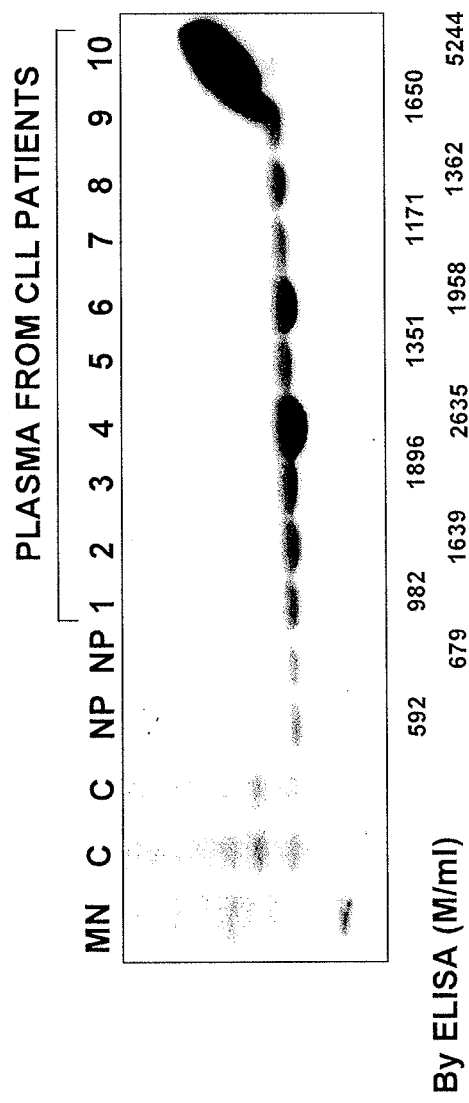
FIG. 1 shows a Western blot demonstrating levels of sCD20 in the plasma of chronic lymphocytic leukemia (CLL) patients. Protein extract from normal peripheral blood mononuclear (MN) cells show no expression of CD20 while leukemic cells from patients with CLL (C) show the expected proteins with molecular weight of 33-36 KD. The plasma from normal individuals (NP) as well as from patients with CLL show the soluble CD20 (sCD20).

The concept of using antibodies in treating cancers or hyperproliferative diseases depend on the ability of the antibodies to reach the tumor cells that express the antigen to which the antibody binds. The presence of free soluble target antigen in the circulation and the possibility of binding and absorbing these antibodies by the cell-free or soluble antigen, and thus preventing these antibodies from reaching the malignant cells, is of concern of the present invention.

The present invention as described herein utilizes therapeutic antibodies to diagnose, monitor or stage hyperproliferative diseases and efficacy of therapy. More particularly, the present invention relates to a method of detecting and monitoring a therapeutic antibody:antigen complex, soluble antigen and soluble therapeutic antibody, wherein a patient has undergone at least one course of immunotherapy.

A variety of hyperproliferative diseases can be monitored, staged or diagnosed according to the methods of the present invention. A hyperproliferative disease includes disease and conditions that are associated with any sort of abnormal cell growth or abnormal growth regulation. Hyperproliferative disease may be further defined as cancer. Yet further, cancer may be defined as a neoplasm or tumor. Exemplary neoplasms that may be monitored or diagnosed using the present invention include, but are not limited to melanoma, non-small cell lung, small-cell lung, lung hepatocarcinoma, retinoblastoma, astrocytoma, gliobastoma, gum, tongue, leukemia, neuroblastoma, head, neck, breast, pancreatic, prostate, renal, bone, testicular, ovarian, mesothelioma, cervical, gastrointestinal, lymphoma, brain, colon, or bladder.

More particularly, the methods of the present invention may be used to monitor, stage or diagnose a hematopoietic neoplasm, for example, but not limited to chronic lymphocytic leukemia, acute myelogenous leukemia, acute lymphoblastic leukemia, myelodysplastic syndrome, chronic myelomonocytic leukemia, juvenile myelomonocyte leukemia, multiple myeloma, lymphoma, T-cell chronic lymphocytic leukemia, prolymphocytic leukemia, lymphomas, B cell related diseases or other T cell related diseases.

Other hyperproliferative diseases contemplated for diagnosing, staging or monitoring are Sjögren's syndrome, rheumatoid arthritis, systemic lupus erythematosus, autoimmune thyroid disease, refractory ocular inflammatory disease, multiple sclerosis, Wegener's granulomatosis and pre-neoplastic lesions in the mouth, prostate, breast, or lung.

It is also envisioned that a combination of soluble markers, soluble antibodies or soluble antibody:antigen complexes may be measured to monitor, stage or diagnosis a hyperproliferative disease. For example, but not limited to, it is envisioned that soluble anti-CD20/CD20 and soluble anti-CD52/CD52 complexes may be measured simultaneously or consecutively to monitor, stage or diagnosis a hyperproliferative disorder.

The presence of circulating target antigens and possible consequent formation of circulating immune complexes may be important for therapeutic approaches based on using antibodies against specific antigens, including Campath-1H (anti-CD52) (Hale et al., 2000; Khorana et al., 2001; Flynn, 2000) or Mylotarg (anti-CD33), (Van Der Vleden et al., 2001) which are also used to treat patients with leukemias. It is contemplated that soluble antigens may bind to the therapeutic antibody in patients receiving the therapeutic antibody to form immune complexes, i.e., antibody:antigen complexes. These immune complexes may reduce the amount of therapeutic antibody from reaching the hyperproliferating cells. Thus, the dosages of the therapeutic antibodies may need to be adjusted accordingly to reach therapeutic levels, such that the antibody is able to reach the target cell having the antigen. Thus, it also is contemplated that the measurement of soluble cell surface antigens and its complexes with therapeutic antibodies may help in designing more effective therapeutic strategies.

Yet further, it is contemplated that the present invention may be used to determine tumor mass. Tumor mass may be determined using the modified sandwich ELISA described herein to measure the levels of soluble leukocyte cell surface antigens, soluble antibodies or soluble antibody:antigen complexes.

A. Cell Surface Antigens

As used herein "target antigen", "surface antigen", "cell surface antigen", or "leukocyte cell surface antigen" are interchangeable and simply refer to the cell surface antigen which is located on the leukocyte, e.g., CD20, CD52, or CD33.

The presence of circulating target antigens and possible consequent formation of circulating immune complexes may be important for other therapeutic approaches based on using antibodies against specific antigens, including, but not limiting to Rituximab (anti-CD20), Campath-1H (anti-CD52) or Mylotarg (anti-CD33).

1. CD20

CD20 is an important molecule in the maturation and proliferation of CD20 positive B-cells (Riley, J. K. et al., 2000). Marked differences in the intensity of CD20 expression in various B-cell malignancies suggest that CD20 may be associated with the different clinical behaviors of the lymphoproliferative disorders (Marti, G. E. et al., 1992 and Ginaldi, L. et al., 1998). It is contemplated that soluble CD20 (sCD20) can be detected in the plasma of both normal individuals and patients with CLL. Yet further, it is contemplated in the present invention that sCD20 may be due to active shedding or to turn-over of cells and fragmentation of the cell membrane or both.

sCD20 may be assessed in plasma, cell lysate or serum. In specific embodiments, sCD20 may be assessed in plasma rather than serum to reduce the risk of the clotting process damaging circulating cells and influencing the levels of sCD20.

The levels of sCD20 may have a direct impact on patients' management and prognosis. sCD20 may play an important role when patients are treated with anti-CD20 (Rituximab). The formation of sCD20/Rituxiamb complexes may reduce the amount of monoclonal antibody that reaches the leukemic cells. If this is a factor, the dosages of the antibodies may need to be adjusted accordingly to reach therapeutic levels, particularly in patients with high levels of sCD20.

2. CD52

Human CD52 (Campath-1H antigen) is an abundant surface molecule on lymphocytes and an important target for therapy of various lymphoproliferative disorders (Tone, M. et al., 1999; Keating, M. J. et al., 1999; Kalil, N. et al., 2000). It comprises a small glycosylphosphatidylinositol (GPI) anchored peptide to which a large carbohydrate moiety is attached (Kirchhoff, C. et al., 2001).

It is contemplated by the inventor that CD52 may shed from cells in a fashion similar to that reported in the male productive system (Kirchhoff, C. et al., 2001). It also is possible that in patients with CLL, the reticuloendothelial system is unable to remove all the cellular debris that result from the turn-over of cells despite the relatively low turn-over rate.

Soluble CD52 (sCD52) may be assessed in plasma, cell lysate or serum. In specific embodiments, sCD52 may be assessed in plasma rather than serum to reduce the risk of the clotting process damaging circulating cells and influencing the levels of sCD52.

Yet further, it also is contemplated in the present invention that the presence of sCD52 may have significant impact on the effectiveness and/or toxicities of Campath-1H therapy. CD52 is considered to be a very appropriate target for monoclonal antibody therapy because of its abundant expression on target cells, its close apposition to the target cell membrane, and low rate of modulation (Treumann, A. et al., 1995; Dyer, M. J. et al., 1999; Bindon, C. I. et al., 1988). The response to Campath-1H is not uniform and the causes of this variability have been examined by a number of investigators. It has been suggested that this variability may partially depend on differences in the level of CD52 expression on target cells (Ginaldi, L. et al., 1998).

3. CD33

CD33 is restricted to the myelomonocytic lineage of cells. CD33 is present on maturing normal hematopoietic cells, however, normal hematopoietic stem cells lack this cell surface antigen. In addition to maturing normal hematopoietic cells, CD33 is also present on acute myelocytic leukemia (AML). Thus, this myeloid cell surface maker has become an attractive target for monoclonal antibody targeting.

Soluble CD33 (sCD33) may be assessed in plasma, cell lysate or serum. In specific embodiments, sCD33 may be assessed in plasma rather than serum to reduce the risk of the clotting process damaging circulating cells and influencing the levels of sCD33.

B. Antibodies

The present invention is directed to the measurement of soluble leukocyte cell surface antigens, soluble antibodies to leukocyte cell surface antigens, or soluble antibody/antigen complexes, and the use of such measurements in the diagnosis and therapy of diseases and disorders.

As used herein, the term "soluble" refers to those molecules that are "spontaneously released"; i.e., released by normal or pathologic physiological processes of the cell, and those molecules present in soluble form in a body fluid by virtue of their in vivo administration to the patient. Such molecules are to be distinguished from "solubilized" cell surface forms of the molecules, whose solubilization is brought about by in vitro manipulation such as cell lysis by detergent. The soluble leukocyte cell surface antigens of the invention are molecules which carry antigenic determinants of their cell-surface counterparts.

The measurement of the soluble molecules of the invention can be valuable in monitoring the effect of a therapeutic treatment on a patient, detecting and/or staging a disease in a patient and in differential diagnosis of the physiological condition of a subject. These measurements can also aid in predicting therapeutic outcome and in evaluating and monitoring the immune status of patients. More than one type of soluble molecule can be measured. The soluble molecules can be measured in any body fluid of the subject including, but not limiting to serum, plasma, urine, saliva, pleural effusions, synovial fluid, spinal fluid, tissue infiltrations and tumor infiltrates.

In certain aspects of the invention, one or more of the antibodies may be a commercially available therapeutic antibody. For example, but not limited to, Rituximab (anti-CD20), Campath-1H (anti-CD52) or Mylotarg (anti-CD33). These antibodies may be used in various diagnostic or therapeutic applications, described herein below.

Yet further, it is also contemplated that one or more antibodies may be produced to the cell surface antigens CD20, CD52 and CD33. It will be understood that polyclonal or monoclonal antibodies specific for the CD20, CD52 and CD33 and related proteins will have utilities in several applications. These include the production of diagnostic kits for use in detecting and diagnosing hyperproliferative disease.

1. Polyclonal Antibodies

Polyclonal antibodies to the CD20, CD52 and CD33 receptors generally are raised in animals by multiple subcutaneous (sc) or intraperitoneal (ip) injections of the CD20, CD52 and CD33 receptors and an adjuvant.

Animals are immunized against the immunogenic composition or derivatives. Animals are boosted until the titer plateaus. The animals are usually bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography.

2. Monoclonal Antibodies

The methods for generating monoclonal antibodies (MAbs) generally begin along the same lines as those for preparing polyclonal antibodies. Rodents such as mice and rats are preferred animals, however, the use of rabbit, sheep, goat, monkey cells also is possible. The use of rats may provide certain advantages (Goding, 1986), but mice are preferred, with the BALB/c mouse being most preferred as this is most routinely used and generally gives a higher percentage of stable fusions.

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies.

The animals are injected with antigen, generally as described above for polyclonal antibodies. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens or lymph nodes. Spleen cells and lymph node cells are preferred, the former because they are a rich source of antibody-producing cells that are in the dividing plasmablast stage.

Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1976), and those using polyethylene glycol (PEG), such as 37% (v/v) PEG. The use of electrically induced fusion methods also is appropriate (Goding, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways.

A sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration.

The individual cell lines could also be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells e.g., normal-versus-tumor cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

3. Humanized Antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., 1986; Riechmann et al., 1988; Verhoeyen et al., 1988), by substituting rodent CDRs or CDR sequences for the corresponding sequences of a human antibody. Accordingly, such "humanized" antibodies are chimeric antibodies wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen.

4. Human Antibodies

Human monoclonal antibodies can be made by the hybridoma method. Human myeloma and mouse-human heteromyeloma cell lines for the production of human monoclonal antibodies have been described in the art (Kozbor, 1984; Brodeur, et al., 1987).

It is now possible to produce transgenic animals (e.g., mice) that are capable, upon immunization, of producing a repertoire of human antibodies in the absence of endogenous immunoglobulin production. For example, it has been described that the homozygous deletion of the antibody heavy chain joining region ($J_H$) gene in chimeric and germline mutant mice results in complete inhibition of endogenous antibody production. Transfer of the human germ-line immunoglobulin gene array in such germ-line mutant mice will result in the production of human antibodies upon antigen challenge. (Jakobovits et al., 1993).

Alternatively, the phage display technology (McCafferty et al., 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle.

5. Antibody Conjugates

The present invention further provides antibodies to CD20, CD52 and CD33 or another secondary antibody for example but not limited to goat anti-human IgG, generally of the monoclonal type, that are linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radio-labeled nucleotides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Any antibody of sufficient selectivity, specificity or affinity may be employed as the basis for an antibody conjugate. Such properties may be evaluated using conventional immunological screening methodology known to those of skill in the art. Sites for binding to biological active molecules in the antibody molecule, in addition to the canonical antigen binding sites, include sites that reside in the variable domain that can bind pathogens, B-cell superantigens, the T cell co-receptor CD4 and the HIV-1 envelope (Sasso et al., 1989; Shorki et al., 1991; Silvermann et al., 1995; Cleary et al., 1994; Lenert et al., 1990; Berberian et al., 1993; Kreier et al., 1991). In addition, the variable domain is involved in antibody self-binding (Kang et al., 1988), and contains epitopes (idiotopes) recognized by anti-antibodies (Kohler et al., 1989).

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. Another such example is the formation of a conjugate comprising an antibody linked to a cytotoxic or anti-cellular agent, and may be termed "immunotoxins".

Antibody conjugates are generally preferred for use as diagnostic agents. Antibody diagnostics generally fall within two classes, those for use in in vitro diagnostics, such as in a variety of immunoassays, and/or those for use in vivo diagnostic protocols, generally known as "antibody-directed imaging".

Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylenediaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

C. Immunodetection Methods

In certain embodiments, the present invention concerns immunodetection methods for binding, purifying, removing, quantifying and/or otherwise generally detecting biological components such as soluble CD20, soluble CD52, soluble CD33, anti-CD22, anti-CD52, anti-CD33, anti-CD20/CD20, anti-CD52/CD52, and anti-CD33/CD33. Some immunodetection methods include enzyme linked immunosorbent assay (ELISA), radioimmunoas say (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle M H and Ben-Zeev O, 1999; Gulbis B and Galand P, 1993; De Jager R et al., 1993; and Nakamura et al., 1987, each incorporated herein by reference.

In general, the immunobinding methods include obtaining a sample suspected of containing a therapeutic antibody:antigen complex, e.g., anti-CD20/CD20, anti-CD52/CD52 and anti-CD33/CD33, or a soluble leukocyte cell surface antigen e.g., CD20, CD52 or CD33, or a soluble antibody, e.g., anti-CD20, anti-CD52, or anti-CD33, contacting the sample with a first monoclonal antibody which captures the complex, and contacting the sample with a composition capable of selectively binding or detecting the complex, e.g., a labeled second antibody, under conditions effective to allow the formation of immunocomplexes. Other examples of compositions capable of selectively binding or detecting the complex include, but are not limited to a antibodies or other ligands that can be labeled using a variety of markers, e.g., biotin/avidin ligand binding arrangement, as is known in the art. One skilled in the art may also use a labeled third antibody.

In terms of antigen, antibody or antibody:antigen complex detection, the biological sample analyzed may be any sample that is suspected of containing an antigen or antibody:complex, such as, for example, a tissue section or specimen, a homogenized tissue extract, a cell, an organelle, separated and/or purified forms of any of the above antigen-containing compositions, or even any biological fluid that comes into contact with the cell or tissue, including blood and/or serum, although tissue samples or extracts are preferred.

Contacting the chosen biological sample with the first antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any anti-CD20/CD20, anti-CD52/CD52 and anti-CD33/CD33 complex or any antigens present i.e., CD20, CD52 or CD33, or any antibodies present i.e., anti-CD20, anti-CD52 or anti-CD33. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241, each incorporated herein by reference. Of course, one may find additional advantages through the use of a secondary binding ligand such as a second antibody and/or a biotin/avidin ligand binding arrangement, as is known in the art. All prior assays to detect immunocomplexes are based on autologous complexes generated by the patients own antibodies and antigen. The present invention is different in that the assays of the present invention detect immunocomplexes as a result of a therapeutic approach.

The antigen, antibody or antigen:antibody complex employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

The immunodetection methods of the present invention have evident utility in the diagnosis and prognosis of conditions such as various diseases wherein a leukocyte cell surface antigens are shed during the disease process, or therapeutic antibodies accumulate in the circulation or therapeutic antibodies form complexes. Here, a biological and/or clinical sample suspected of containing soluble leukocytes cell surface antigens, e.g., CD20, CD52, CD33, soluble therapeutic antibodies, e.g., anti-CD20, anti-CD52, anti-CD33 or therapeutic antibody:antigen complexes e.g., anti-CD20/CD20, anti-CD52/CD52 or anti-CD33/CD33 are measured.

In the clinical diagnosis and/or monitoring of patients with various forms a hyperproliferative disease, such as, for example, cancer, the alteration in the levels of a soluble leukocytes markers, soluble therapeutic antibodies and soluble therapeutic antibody:antigen complexes in comparison to the levels in a corresponding biological sample from a normal subject is indicative of a patient with cancer or other hyperproliferative diseases. However, as is known to those of skill in the art, such a clinical diagnosis would not necessarily be made on the basis of this method in isolation. Those of skill in the art are very familiar with differentiating between differences in types and/or amounts of biomarkers, which represent a positive identification, and/or low level and/or background changes of biomarkers. Indeed, background levels are often used to form a "cut-off" above which increased detection will be scored as significant and/or positive.

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In one exemplary ELISA, antibodies of the leukocyte cell surface antigen (e.g., anti-CD20, anti-CD33, anti-CD52) are immobilized onto a selected surface exhibiting protein affinity, such as a well in a polystyrene microtiter plate. Then, a sample from a patient that has undergone at least one course, e.g., one injection, of immunotherapy with a therapeutic antibody, e.g., Rituxiamb, Campath-H or Mylotarg is added to the wells. After binding and/or washing to remove non-specifically bound immune complexes, the bound therapeutic antibody:antigen complex may be detected. Detection is generally achieved by the addition of second antibody that is linked to a detectable label. This type of ELISA is a simple "sandwich ELISA".

In another exemplary sandwich ELISA used to detect the therapeutic antibody, the antibody of the leukocyte cell surface antigen is immobilized onto the well surface. Next, cell lysate from a patient that has undergone at least one course, e.g., one injection, of immunotherapy with a therapeutic antibody is added to the wells. The cell lysate contains an antigen that binds to the antibody. Then, plasma from the patient is added to the well. The plasma contains the therapeutic antibody which will bind to the antigen. After binding and/or washing to remove non-specifically bound immune complexes, the bound therapeutic antibody:antigen complex may be detected. Detection is achieved by the addition of a third antibody that is linked to a detectable label.

In yet another exemplary sandwich ELISA used to detect the leukocyte antigen, the antibody of the leukocyte cell surface antigen is immobilized onto the well surface. Next, plasma from a patient that has undergone at least one course, e.g., one injection, of immunotherapy with a therapeutic antibody is added to the wells. After binding and/or washing to remove non-specifically bound immune complexes, the bound therapeutic antibody:antigen complex may be detected. Then, a second antibody that is linked to a detectable label is added. The second antibody is typically the therapeutic antibody which has been labeled.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure.

Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

It also is contemplated that the above reagents may be packaged in a kit that may be produced commercially to measure the soluble antigens, antibodies or antibody:antigen complexes described herein.

D. Immunotherapy

In specific embodiments of the present invention, it is provided that the patient has undergone at least one course, e.g., one injection, of immunotherapy. As described herein, immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In specific embodiments, the antibody that is used for the immunotherapy is Rituximals, Campath-1H, or Mylotarg.

Immunotherapy could also be used as part of a combined therapy. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine pro-apoptotic effect with immune stimulatory effects. Immune stimulating molecules also exist including: cytokines such as IL-2, IL-4, IL-12, GM-CSF, gamma-IFN, chemokines such as MIP-1, MCP-1, IL-8 and growth factors such as FLT3 ligand.

As discussed earlier, examples of immunotherapies currently under investigation or in use are immune adjuvants (e.g., *Mycobacterium bovis, Plasmodium falciparum*, dinitrochlorobenzene and aromatic compounds) (U.S. Pat. No. 5,801,005; U.S. Pat. No. 5,739,169; Hui and Hashimoto, 1998; Christodoulides et al., 1998), cytokine therapy (e.g., interferons α, β and γ; IL-1, GM-CSF and TNF) (Bukowski et al., 1998; Davidson et al., 1998; Hellstrand et al., 1998) gene therapy (e.g., TNF, IL-1, IL-2, p53) (Qin et al., 1998; Austin-Ward and Villaseca, 1998; U.S. Pat. No. 5,830,880 and U.S. Pat. No. 5,846,945) and monoclonal antibodies (e.g., anti-ganglioside GM2, anti-HER-2, anti-p185) (Pietras et al., 1998; Hanibuchi et al., 1998; U.S. Pat. No. 5,824,311). Herceptin (trastuzumab) is a chimeric (mouse-human) monoclonal antibody that blocks the HER2-neu receptor. It possesses anti-tumor activity and has been approved for use in the treatment of malignant tumors (Dillman, 1999).

1. Passive Immunotherapy

A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

Preferably, human monoclonal antibodies are employed in passive immunotherapy, as they produce few or no side effects in the patient. However, their application is somewhat limited by their scarcity and have so far only been administered intralesionally. Human monoclonal antibodies to ganglioside antigens have been administered intralesionally to patients suffering from cutaneous recurrent melanoma (Irie & Morton, 1986). Regression was observed in six out of ten patients, following, daily or weekly, intralesional injections. In another study, moderate success was achieved from intralesional injections of two human monoclonal antibodies (Irie et al., 1989).

It may be favorable to administer more than one monoclonal antibody directed against two different antigens or even antibodies with multiple antigen specificity. Treatment protocols also may include administration of lymphokines or other immune enhancers as described by Bajorin et al. (1988). The development of human monoclonal antibodies is described in further detail elsewhere in the specification.

2. Active Immunotherapy

In active immunotherapy, an antigenic peptide, polypeptide or protein, or an autologous or allogenic tumor cell composition or "vaccine" is administered, generally with a distinct bacterial adjuvant (Ravindranath & Morton, 1991; Morton & Ravindranath, 1996; Morton et al., 1992; Mitchell et al., 1990; Mitchell et al., 1993). In melanoma immunotherapy, those patients who elicit high IgM response often survive better than those who elicit no or low IgM antibodies (Morton et al., 1992). IgM antibodies are often transient antibodies and the exception to the rule appears to be anti-ganglioside or anticarbohydrate antibodies.

3. Adoptive Immunotherapy

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). To achieve this, one would administer to an animal, or human patient, an immunologically effective amount of activated lymphocytes in combination with an adjuvant-incorporated anigenic peptide composition as described herein. The activated lymphocytes will most preferably be the patient's own cells that were earlier isolated from a blood or tumor sample and activated (or "expanded") in vitro. This form of immunotherapy has produced several cases of regression of melanoma and renal carcinoma, but the percentage of responders were few compared to those who did not respond.

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

E. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Patient Samples

Plasma samples were collected from patients with CLL and normal individuals. Peripheral blood samples were collected in EDTA tubes. The diagnosis of CLL was established based on morphologic, immunologic and molecular evaluation of peripheral blood and bone marrow. Immunologic evaluation included flow cytometric analysis of leukemic cells using CD19, CD5, CD20, CD23, CD11C, CD22, FMC-7, CD79B, CD3, CD4, CD8, kappa and lambda. Molecular studies included immunoglobulin and T-cell receptors genes as well as Bcl-1 and Bcl-2 rearrangement studies.

Example 2

Western Blot Analysis of Plasma and Cellular CD20

Five microliter of plasma from normal and CLL patients were electrophoretically separated on 9.5 SDS-PH gels. Cell lysates from normal mononuclear cells and CLL cell samples were used as positive and negative controls. The nitrocellulose membrane was blocked with 5% non-fat milk in PBS containing 0.1% Tween 20 and 0.01% sodium azide for 6-8 hours at room temperature. The blots were incubated overnight at 4° C. with 1 μg/μl mouse anti-CD20 antibody (Sigma Chemical Corporation, St. Louis, Mo.) and PBS containing 2.5% non-fat milk, 2.5 bovine serum albumin (BSA) and 0.1% Tween 20. The membrane was then washed with PBS containing 0.1% Tween 20. The blot was then incubated with 1:20 diluted anti-mouse horseradish peroxidase-conjugated Ig (Sigma Chemical Corporation, St. Louis, Mo.) and PBS containing 1% non-fat milk and 0.1% tween 20. Immunoreactive bands were developed using the ECL detection system (Amersham, Arlington Heights, Ill.).

As shown in FIG. 1, reactive bands with anti-CD20 were detected in the plasma of patients with CLL at high levels. The detected soluble (sCD20) bands in the plasma correspond to the 35 kD CD20 that was detected in CLL cells. Plasma from normal individuals also showed low levels of sCD20. CLL cells showed easily detectable CD20 protein, but mononuclear cells from normal individuals, which are richer with monocytes and T-cells and contain few B-cells, showed no detectable CD20 bands.

Example 3

Western Blot Analysis of Plasma and Cellular CD52

Exactly 14.5 ul of total plasma from patients and 40 microgram of cellular protein were electrophoresed on 9.5 SDS-PAGE gels. Cell lysates from normal mononuclear cells and CLL cell samples were used as positive and negative controls. The protein was transferred into nitrocellulose membranes using standard techniques. Membranes were blocked with 5% non-fat milk in PBS containing 0.1% Tween-20 and 0.01% of sodium azide for 6 to 8 hours at warm temperature. The blots were incubated overnight at 4° C. with 1 ug anti-CD52 (Campath-1G) antibodies and PBS containing 2.5 non-fat milk, 2.5 bovine serum albumin (BAS) and 0.01 Tween 20. The membranes were then washed with PBS containing 0.01% Tween 20. The blots were then incubated with Tween 20 diluted goat anti-rat Ig linked to horseradish peroxidase (Sigma Chemical Corporation, St. Louis, Mo.) and PBS containing 1% non-fat milk and 0.1% Tween 20. Radio-active bands were developed using ECL detection system (Amersham, Arlington Heights, Ill.).

Figure 2:
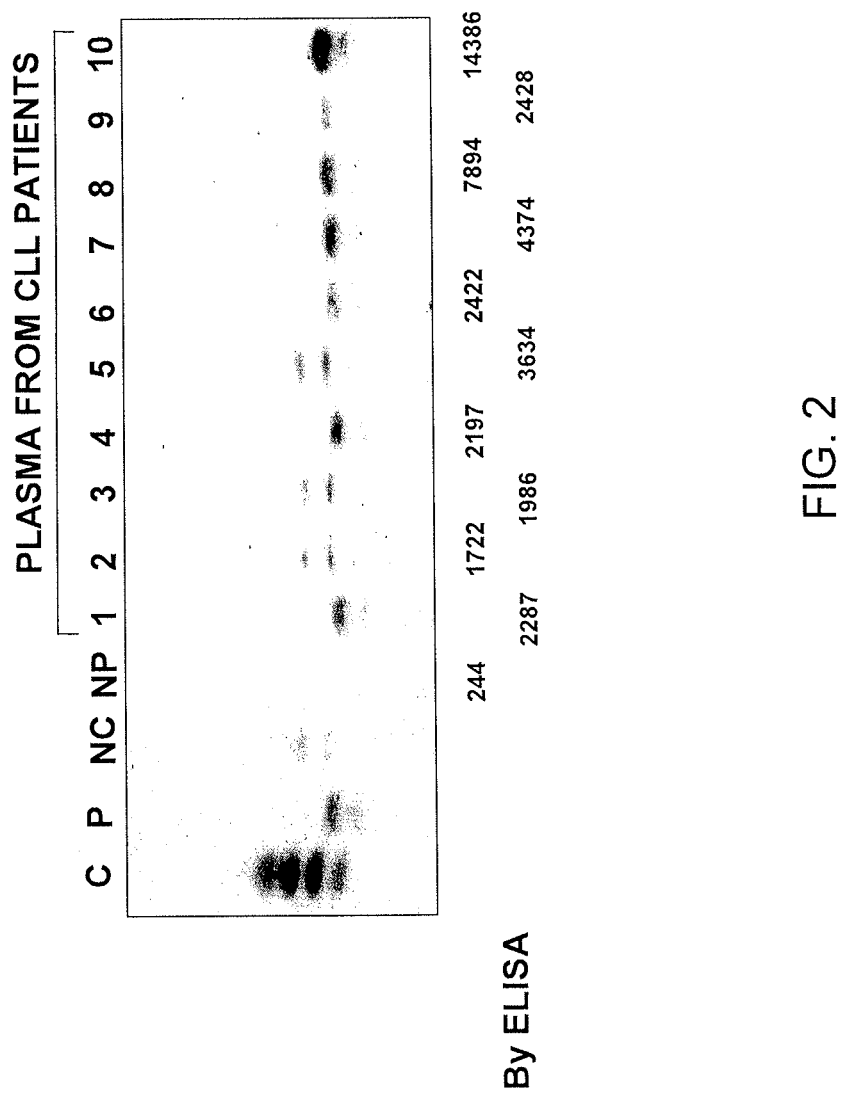
FIG. 2 shows a Western blot demonstrating levels of sCD52 in the plasma of CLL patients. Protein extract from leukemic cells (C) show the expected proteins and the plasma from the same patient (P) show the soluble sCD52. CD52 is also detected in protein extract from peripheral blood mononuclear cells from normal individual (NC) as well as in normal plasma (NP).

As shown in FIG. 2, protein extracts from leukemic cells show the expected 14 to 20 kD CD52 glycoproteins as detected using Campath-1G monoclonal antibody. Plasma from the same patient showed corresponding bands.

Example 4

ELISA Analysis of Plasma and Cellular CD20

An ELISA assay for detecting sCD20 in the plasma of patients was developed. Briefly, a 96-well polystyrene microplate was coated with capturing antibody for CD20 purchased from Sigma. Plates were then washed 6 times with PBS containing 0.01% Tween 20, blocked with BSA in PBS containing 0.01% Tween 20 for 1 to 3 hours at 37° C., washed in PBS containing 0.01% Tween 20. 100 microliter of plasma was added to the wells. The mixture was then incubated at room temperature for two hours. The sCD20 was detected using humanized anti-CD20 (Rituximab) antibody after horseradish peroxidase-enzyme conjugation using standard technique; Rituximab was diluted 1:400 in 2% BSA 0.01% Tween 20. The plates were incubated for twelve hours. The wells were then washed 6 times with PBS containing 0.01% Tween 20. 100 units of substrate were added for the development of the color and incubated for 15 to 30 minutes with constant shaking. The reaction was then stopped with 15 microliters of sodium chloride, the plates were read at 450 nm wavelength. Serial dilution of known number of molecules of synthetic CD20 peptide was used to generate a standard curve.

Figure 3:
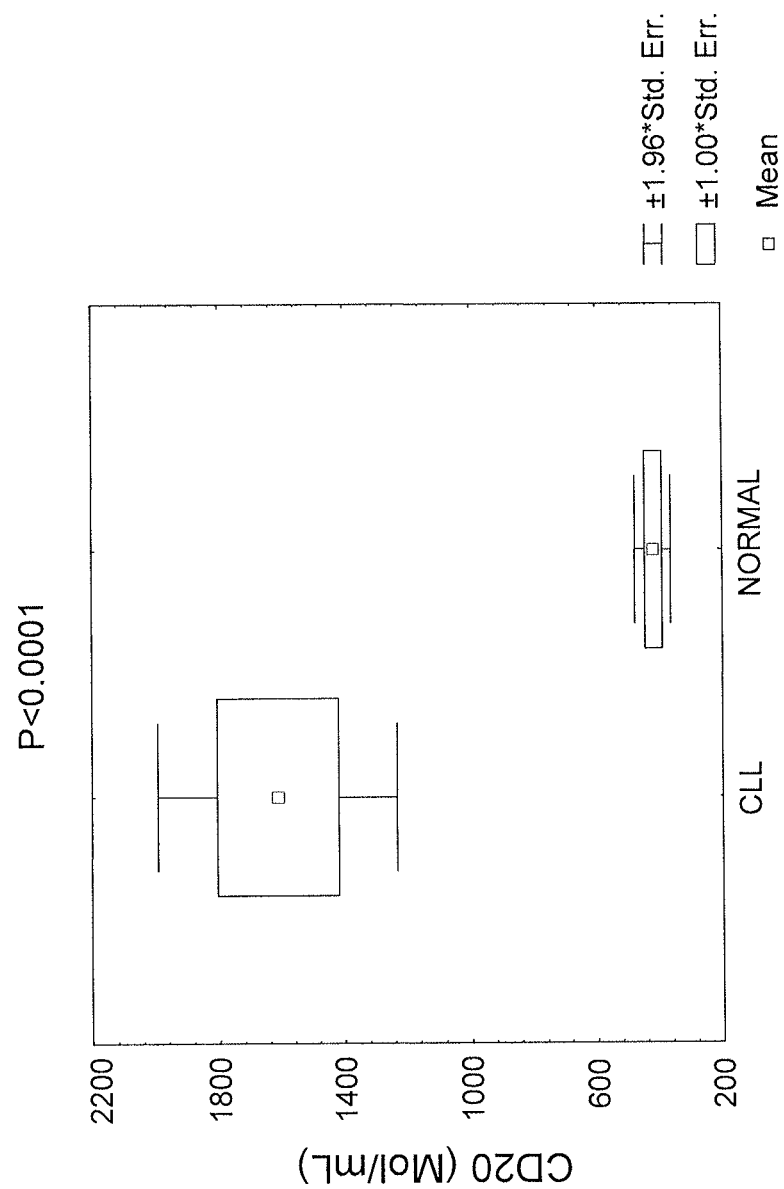
FIG. 3 shows higher levels of sCD20 in patients with CLL as compared with normal individuals.

The intensity of the CD20 bands on the Western blot correlated with the levels seen on the ELISA assay as shown in FIG. 1. Dilutions and measurements of diluted samples showed almost identical values. Levels of sCD20 in the plasma of CLL patients as detected by ELISA assay were significantly higher than those detected in 31 normal individuals. (FIG. 3). sCD20 levels in patients with CLL varied from 52.89 to 15740 M/ml (median=776.9). In contrast the levels of sCD20 in the plasma of normal individuals varied between 123.55 to 547.10 M/ml (median=470).

Example 5

SCD52 Enzyme Linked Immunoabsorbant (ELISA) Assay

An ELISA assay for detecting the sCD52 in the plasma of patients was developed. Briefly, 96-well polystyrene microtiter plates were coated with Campath-1M antibodies. Plates were then washed 6 times with PBS containing 0.01% Tween 20, blocked with BSA in PBS containing 0.01% Tween 20 for 1 to 3 hours at 37° C., washed in PBS containing 0.01% Tween 20. 100 ul of patient's plasma was added and incubated for 3 hours, then washed 8 times with PBS containing 0.01% Tween 20. The sCD52 was detected using the humanized anti-CD52 Campath-1H after horseradish peroxides labeling using standard techniques; the Campath-1H was diluted 1:400 in 2% BSA 0.01% Tween 20. The wells were then washed 6 times with PBS containing 0.01% Tween 20. 100 units of substrate were added for the development of the color and incubated for 15 to 30 minutes with constant shaking. The reaction was then stopped with 15 microliters of sodium chloride, the plates were read at 450 nm wavelength.

Figure 4:
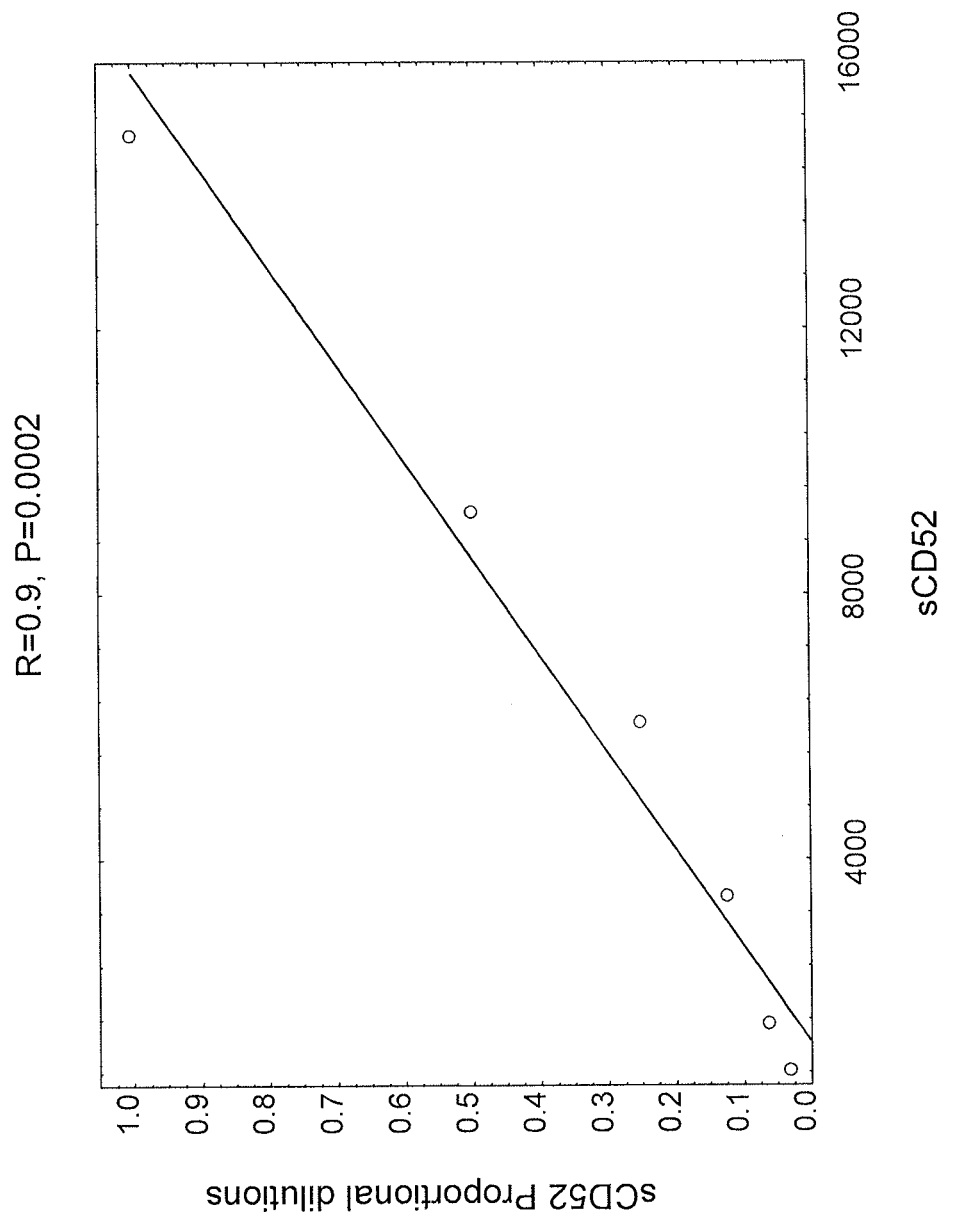
FIG. 4 illustrates the linearity of sCD52 determined by ELISA.
Figure 5:
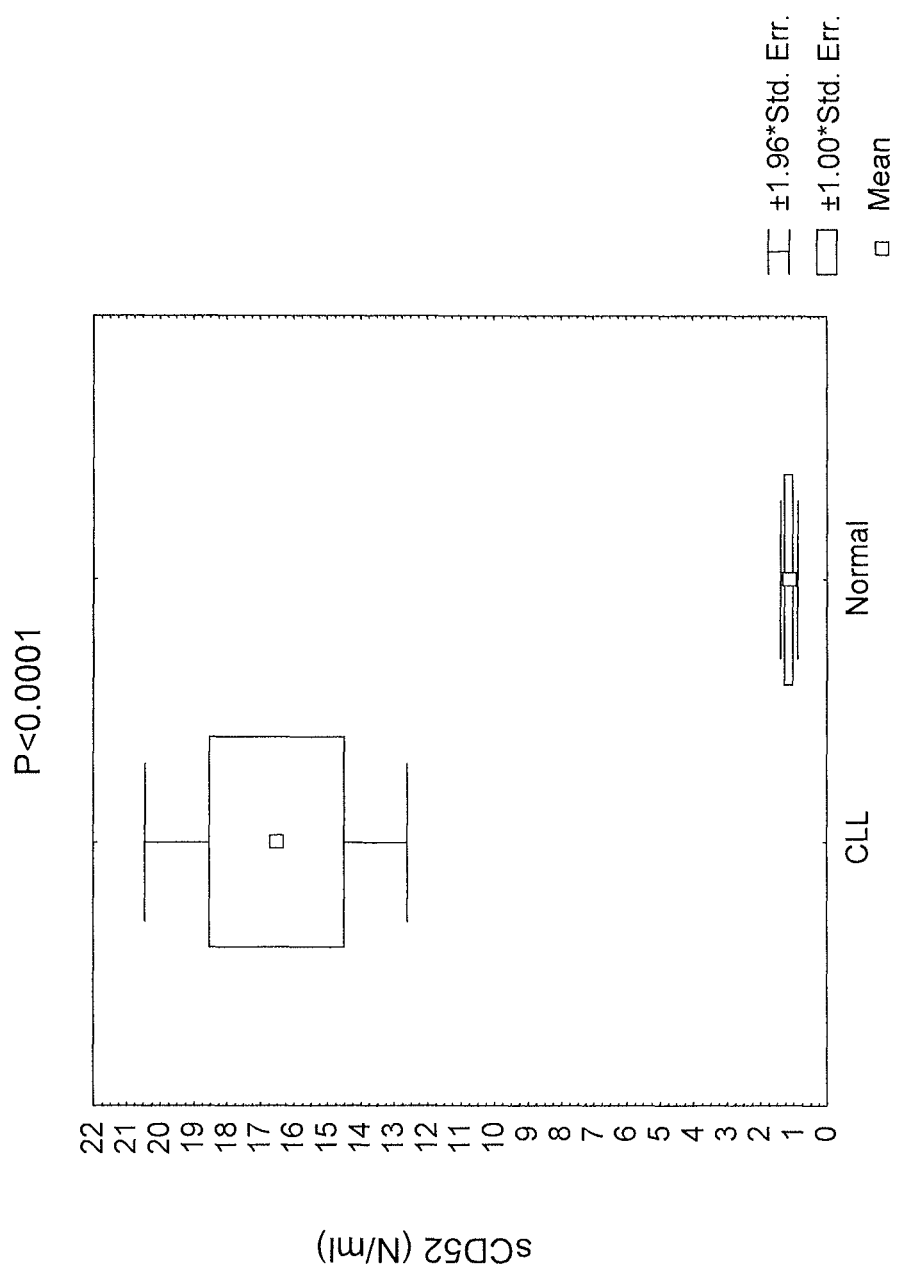
FIG. 5 illustrates that CLL patients have higher levels of sCD52 as compared with normal individuals.

The levels detected in the ELISA were normalized to those detected in 25 normal individuals. The median level detected in the 25 normal individuals was assigned a value of 1 and the levels detected in the plasma of CLL patients are expressed as folds of the normal median of normals. As shown in FIG. 2, the ELISA levels appear to correlate with the levels detected on the western blot. The Western blot bands were scanned and quantified. Equal amounts of plasma from all samples were run on the gel. In order to verify the linearity of the ELISA, dilutions of plasma from a patient with high level and correlated the measurements with dilutions. As shown in FIG. 4, there was complete correlation between the dilutions and the levels detected by the ELISA. As shown in FIG. 5, upon comparing the sCD52 levels detected in the normal patients with those in CLL patients there was significant increase in the levels of CD52 in CLL patients.

Example 6

Plasma CD20/Rituximab Complexes (ELISA)

sCD20/Rituximab complexes formation was investigated in the plasma of CLL patients treated with Rituximab using an ELISA assay.

Figure 6:
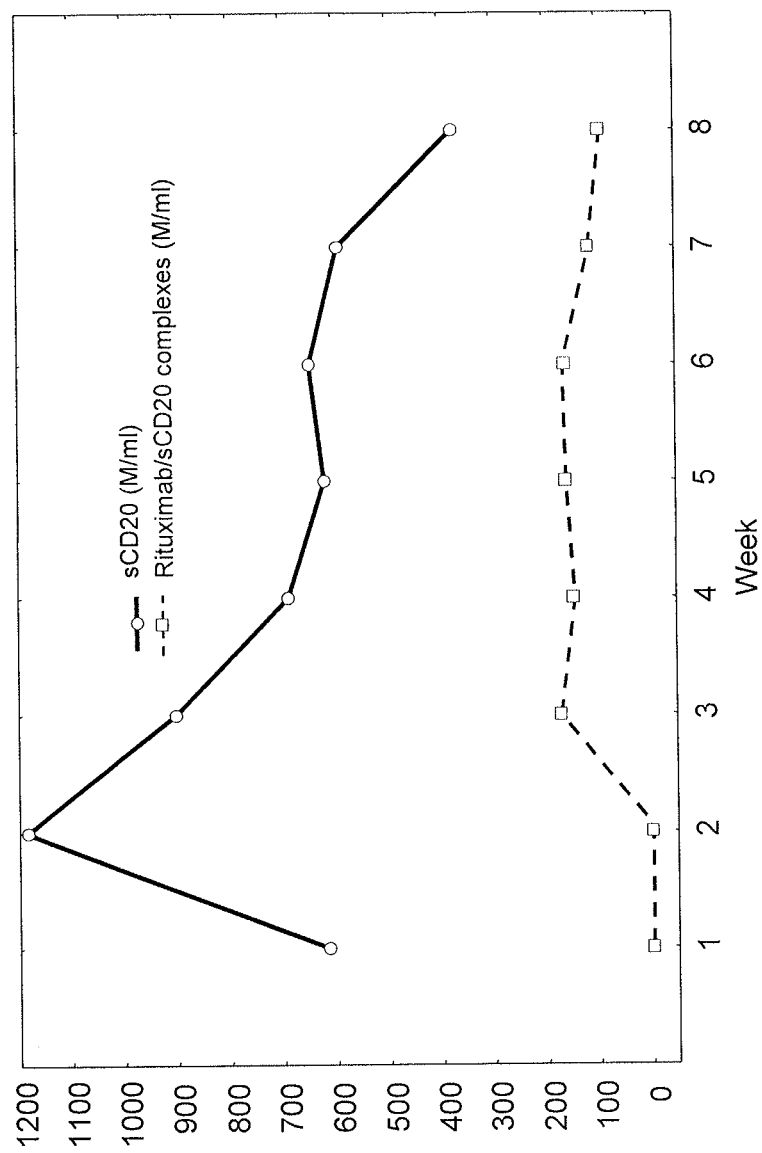
FIG. 6 shows that the sCD20/Rituximab complexes increased with an increase in the levels of Rituximab.

The plasma CD20/Rituximab complexes were measured using a similar sandwich ELISA assay. Briefly, a 96-well polystyrene microplate was coated with capturing antibody for CD20 and washed as described above. Plasma samples were added after 1:100 dilution in PBS and incubated as described above. For detection, goat anti-human immunoglobulin that was horseradish peroxidase conjugated was used. The wells were then washed 6 times with PBS containing 0.01% Tween 20. 100 units of substrate were added for the development of the color and incubated for 15 to 30 minutes with constant shaking. The reaction was then stopped with 15 microliters of sodium chloride, the plates were read at 450 nm wavelength. Serial dilution of known number of molecules of synthetic CD20 peptide after binding at saturation to Rituximab was used to generate a standard curve.

sCD20/Rituximab immune complexes were detected in all 20 single samples from 20 CLL patients being treated with Rituximab. The ELISA assay showed linear correlation between dilutions of known amount of synthetic peptide mixed with excess Rituximab (R=1). Immune complexes were detected in serial samples from a patient being treated with Rituximab (FIG. 6). As shown in FIG. 6, sCD20/Rituximab complexes increased with an increase in the levels of the Rituximab.

Example 7

High Levels of sCD20 Correlate with Advanced Stage of CLL

The correlation of plasma levels of sCD20 in 180 CLL patients with various characteristics and clinical stages of the disease was assessed. The characteristics of the patients studied are listed in Table 1.

Figure 7:
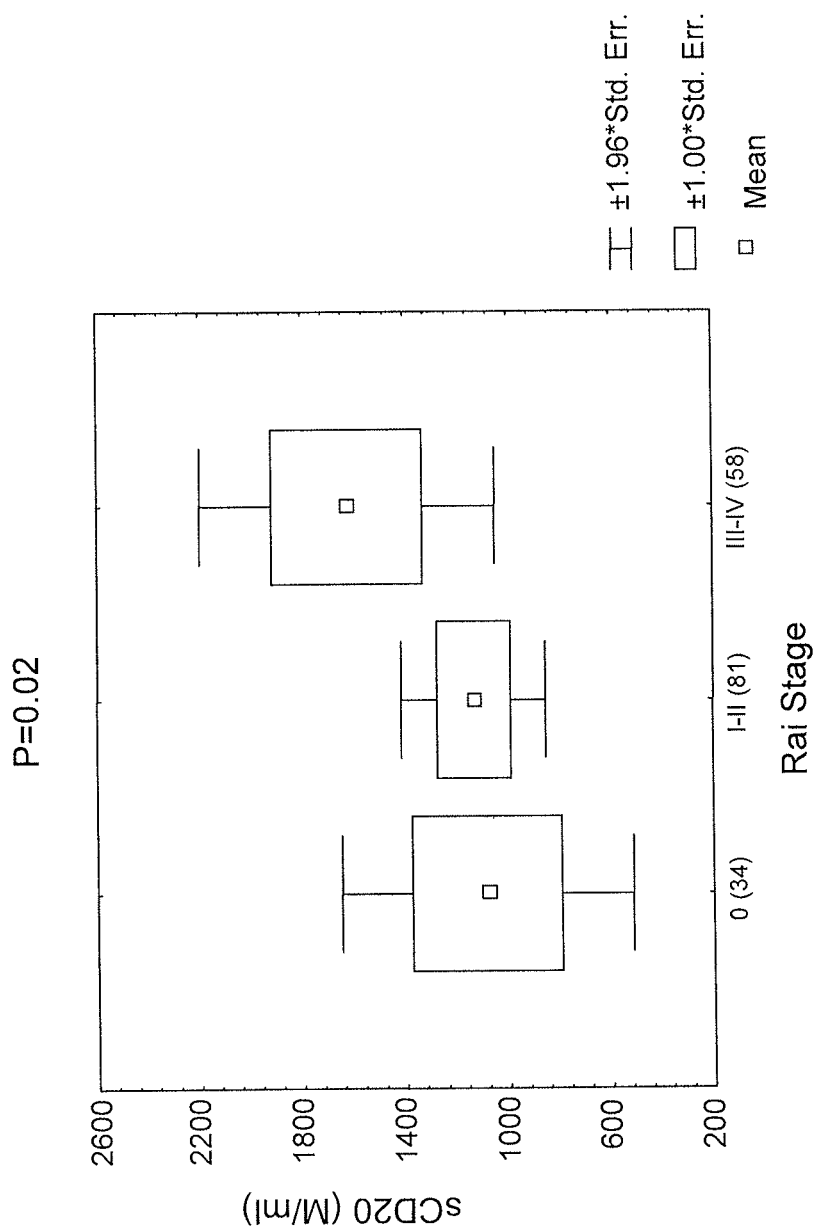
FIG. 7 shows the direct correlation between sCD20 levels and Rai staging.
Figure 8:
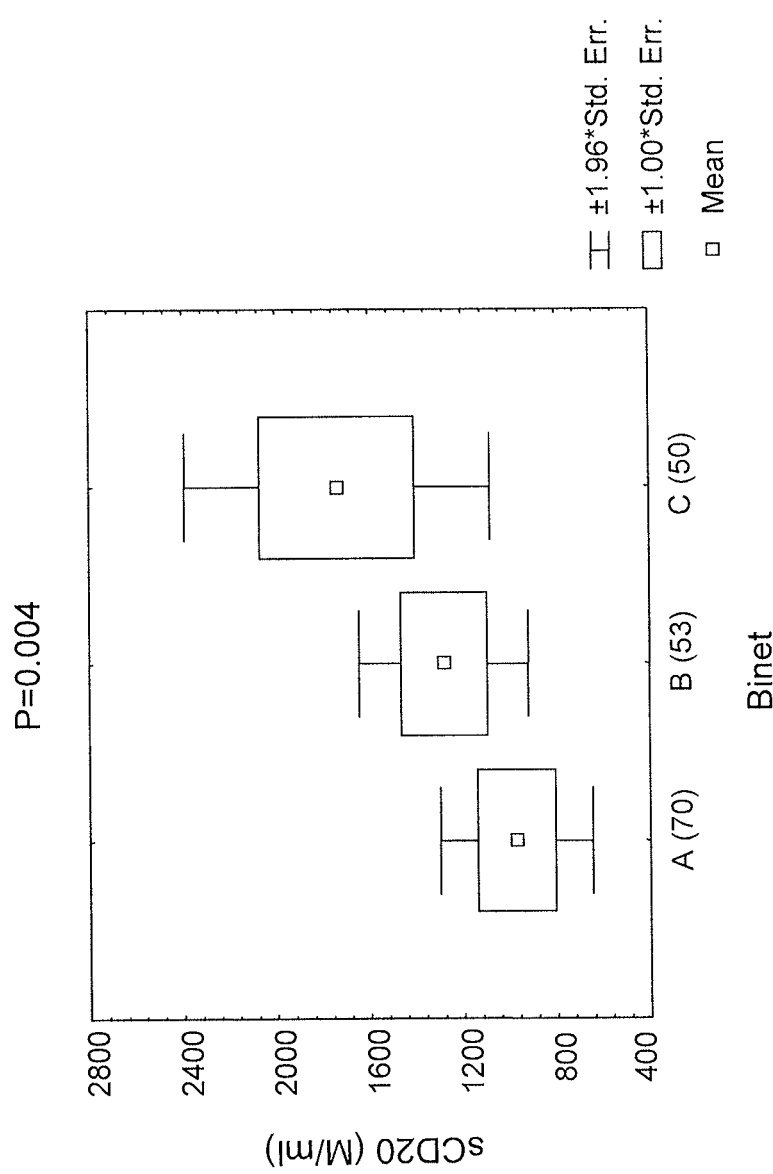
FIG. 8 shows a direct correlation between sCD20 levels and Binet staging.

Thirty two (17.8%) of the patients had Rai stage 0 disease, 81 (45%) stage I-II, and 60 (33%) in stage III-IV. The median age of the patients was 61 and median level of $\beta_2 M$ was 3.4. There was no significant difference in sCD20 levels between males and females (p-value=0.66). sCD20 levels were highly correlated with $\beta_2 M$ (r=0.23, p-value=0.006), platelet count (r=−0.22, p-value=0.004), percentage of CD19+/CD38+ cells (r=0.20, p-value=0.03) and hemoglobin level (r=−0.18, p-value=0.02)(Table 2). sCD20 levels did not significantly correlate with white blood count (r=−0.07, p-value=0.33), lymphocyte count (r=−0.03, p-value=0.71) or age (r=0.05, p-value=0.53). There was a direct correlation between sCD20 levels and Rai stages. When cases were grouped as Rai 0, Rai I-II, and Rai higher Rai stages had significantly higher levels of sCD20 (P=0.01, Kruskal-Wallis test) (FIG. 7). Patients in Rai stages 0-II had significantly lower sCD20 levels as compared to patients with Rai stages III-IV (P=0.01). Similar results were obtained when Binet staging was used (P=0.004) (FIG. 8). There was no correlation between sCD20 levels and number of sites of lymphadenopathy (P=0.11) or hepatomegaly (P=0.25).

TABLE 1

Patient Characteristics (N = 180)

| Variable | Median (range) | N (%) |
|---|---|---|
| Sex | | |
| Male | | 116 (65) |
| Female | | 63 (35) |
| Rai | | |
| 0 | | 32 (17.8) |
| 1 | | 51 (29.5) |
| 2 | | 30 (16.7) |
| 3 | | 15 (8.3) |
| 4 | | 45 (25.0) |

TABLE 1-continued

Patient Characteristics (N = 180)

| Variable | Median (range) | N (%) |
|---|---|---|
| Parameter (median/range) | | |
| Age in years | 61 (33~84) | |
| CD38+/CD19+ (%) | 7.7 (0.3~98) | |
| Hemoglobin g/dl | 12.8 (4~17.8) | |
| Platelets × 10³/ul | 142 (4~342) | |
| WBC × 10³/ul | 55.9 (1.4~333.9) | |
| Lymphocytes (%) | 85 (9~99) | |
| $\beta_2 M$ mg/L | 3.4 (1.3~12.7) | |
| sCD20 M/ml | 776.9 (52.89~15740) | |

TABLE 2

Correlation of sCD20 with clinical parameters in patients with CLL

| Variable | P-value (R-value) |
|---|---|
| Hgb | 0.02 (−0.18) |
| β2m | 0.006 (0.23) |
| RAI (0, I-II, III-IV) | 0.01 (Kruskal-Wallis) |
| Binet (A, B, C) | 0.004 (Kruskal-Wallis) |
| Platelets | 0.004 (−0.22) |
| % CD19+/CD38+ | 0.03 (0.20) |
| Splenomegaly | 0.07 |
| Hepatomegaly | 0.25 |
| Node Enlargement | 0.11 |
| Age | 0.53 (0.05) |
| Lymphocytes | 0.71 (−0.03) |
| WBC | 0.33 (−0.07) |
| Sex | 0.66 |

TABLE 3

Univariate Cox Proportional Hazards Model (N = 180)

| Variable | Coefficient | Relative Risk | P-value |
|---|---|---|---|
| Hemoglobin | −0.241 | 0.79 | 0.0005 |
| Log($\beta_2 M$) | 2 | 7.37 | 0.0005 |
| RAI | 0.353 | 1.42 | 0.018 |
| RAI = 3, 4 (vs 0, 1, 2) | 0.995 | 2.71 | 0.021 |
| Platelets | −0.008 | 0.99 | 0.020 |
| Log(CD38+/CD19+) | 0.551 | 1.73 | 0.023 |
| sCD20 | 0.0002 | 1.00 | 0.006 |
| Log(sCD20) | 0.374 | 1.45 | 0.080 |
| sCD20 >= 1875 | 1.11 | 3.03 | 0.020 |
| Age | 0.025 | 1.02 | 0.22 |
| Log(%-lymphocytes) | 0.24 | 1.27 | 0.32 |
| Log(WBC) | 0.183 | 1.2 | 0.43 |
| Sex = male | −0.13 | 0.88 | 0.76 |

Figure 9:
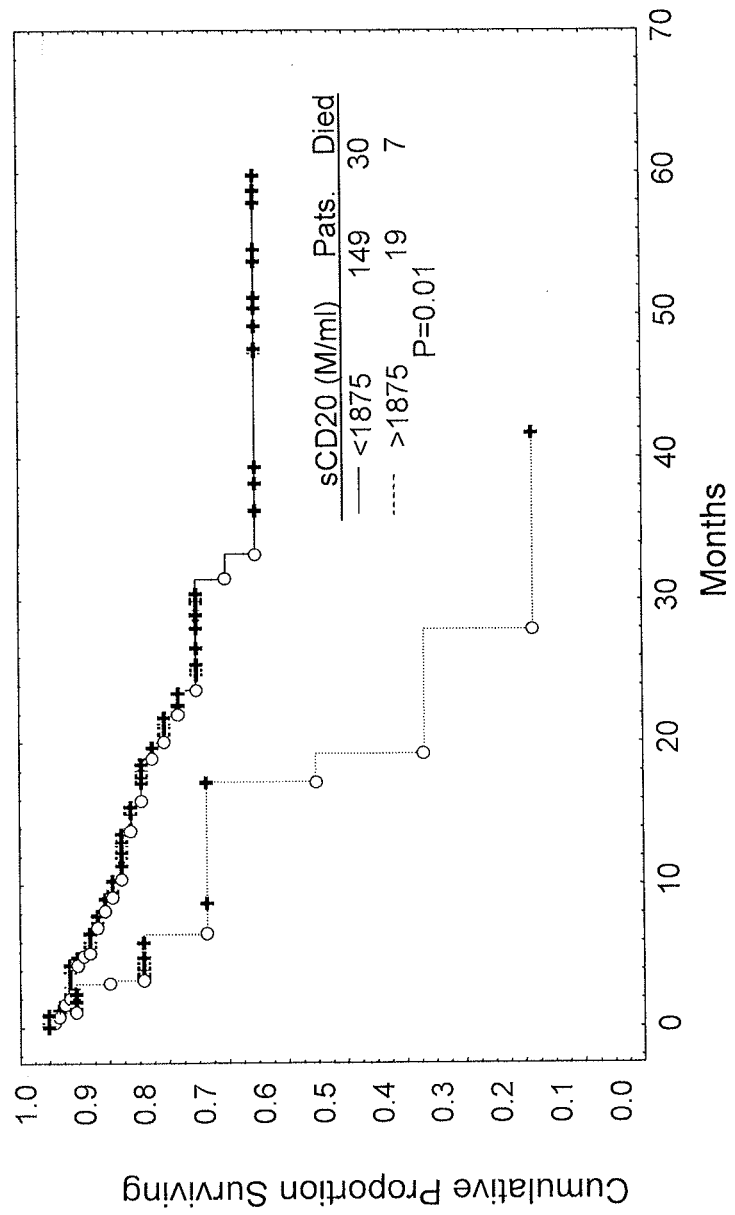
FIG. 9 shows the median survival of patients with high sCD20 compared to patients with low sCD20.

Univariate Cox proportional hazards model was fitted (Table 3) to test for variable that predicts survival in this patient group. As shown in Table 3, the expression of CD38, hemoglobin, platelets, $\beta_2 M$, Rai staging, and sCD20 were all predictors of survival. sCD20, as a continuous variable in Cox regression model, was a predictor of survival (P=0.002). However, in light of the martingale residual plot for goodness of fit, log transformation was needed in order to fit sCD20 better to the model. When the logarithmic of sCD20 was used to re-fit the univariate Cox model, it was only marginally significant with p-value 0.08. Therefore sCD20 was dichotomized using a cut off point of 1875 M/ml chosen by CART, which demonstrated two groups of patients with significantly different survival profiles. Patients with sCD20>1875 M/ml had significantly shorter survival times than those with sCD20<=1875 M/ml (P=0.01) (FIG. 9). Median survival in the patients with high sCD20 was approximately 18 months while the median in those with lower sCD20 levels had not been reached (FIG. 9). Multivariate analysis showed that this shorter survival in patients with sCD20>1875 M/ml was independent of Rai stage or hemoglobin.

The levels of sCD20 may have a direct impact on patients' management and prognosis. The levels of sCD20 correlated directly with Rai and Binet stages, and $\beta_2M$ and negatively with platelets and hemoglobin. sCD20 did not correlate with white cell count, age, splenomegaly, or lymph node enlargement. High levels of sCD20 correlated with shorter survival independently from the Rai staging. This suggested that sCD20 levels may reflect a specific clinical stage of the disease as well a specific biology. sCD20 may play an important role when patients are treated with anti-CD20 (Rituximab). The formation of sCD20/Rituxiamb complexes may significantly reduce the amount of monoclonal antibody from reaching the leukemic cells. If this is a factor, the dosages of the antibodies may need to be adjusted accordingly to reach therapeutic levels, particularly in patients with high levels of sCD20. The measurement of sCD20 and its complexes with therapeutic antiCD20 antibodies may help in designing more effective therapeutic strategies.

Example 10

Figure 10:
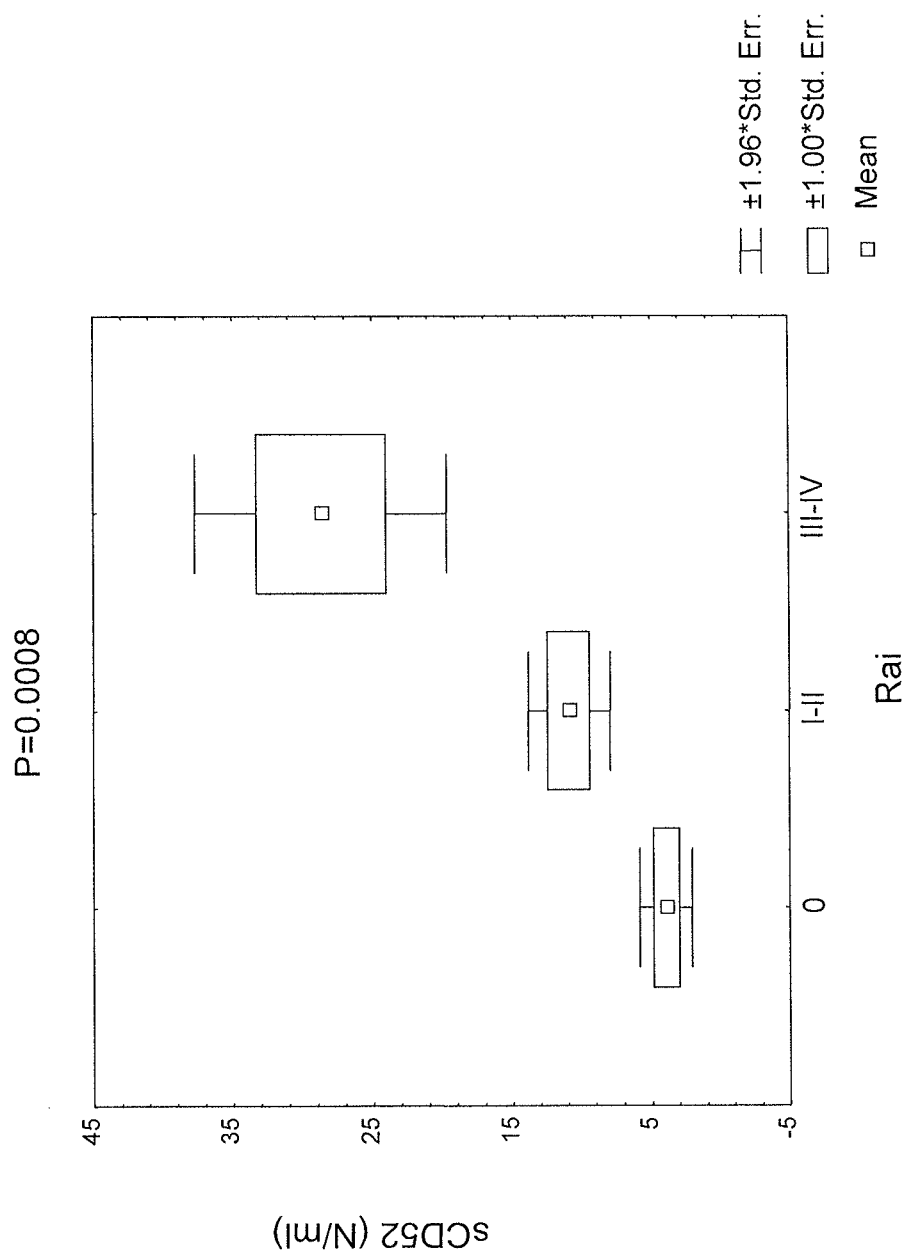
FIG. 10 shows that the levels of sCD52 correlate with Rai staging.
Figure 11:
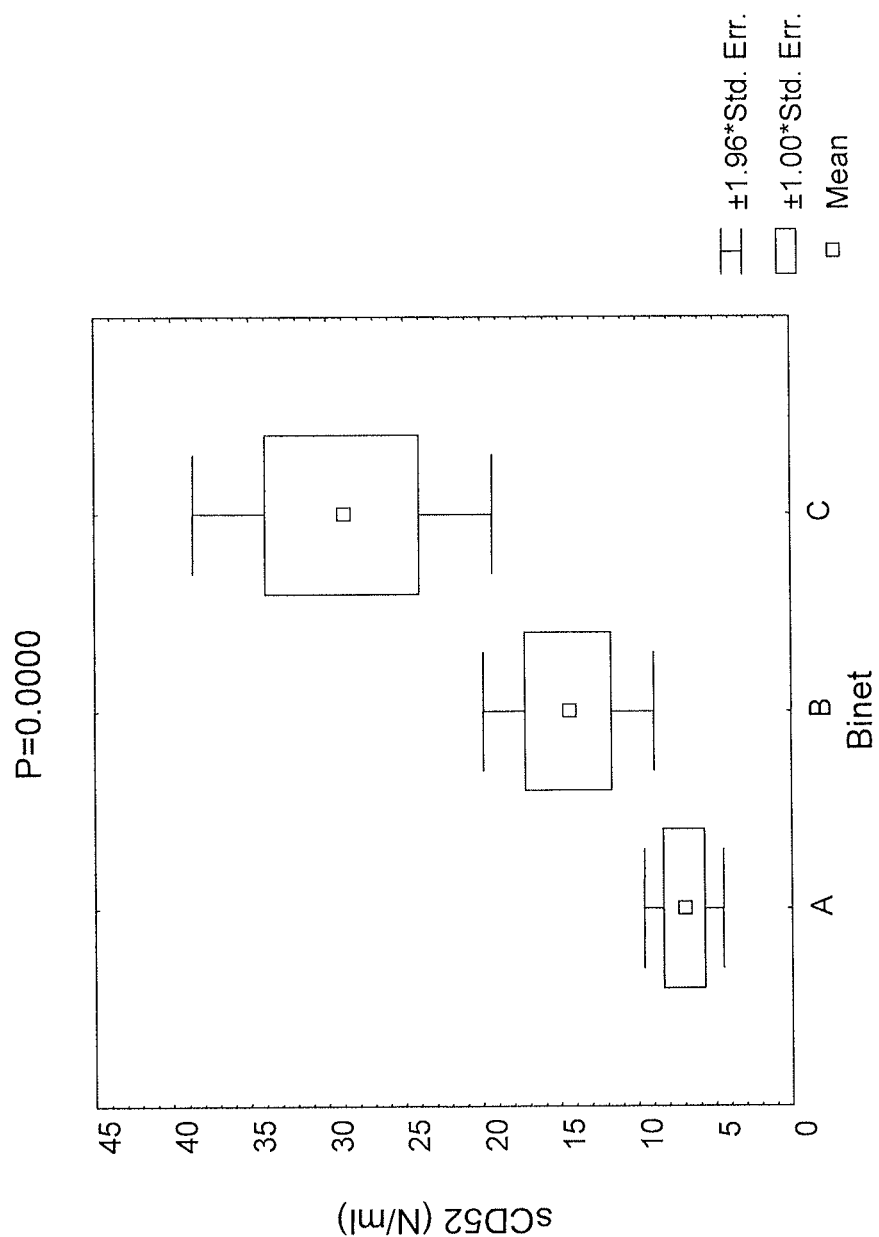
FIG. 11 shows the levels of sCD52 correlate with Binet staging.
Figure 12:
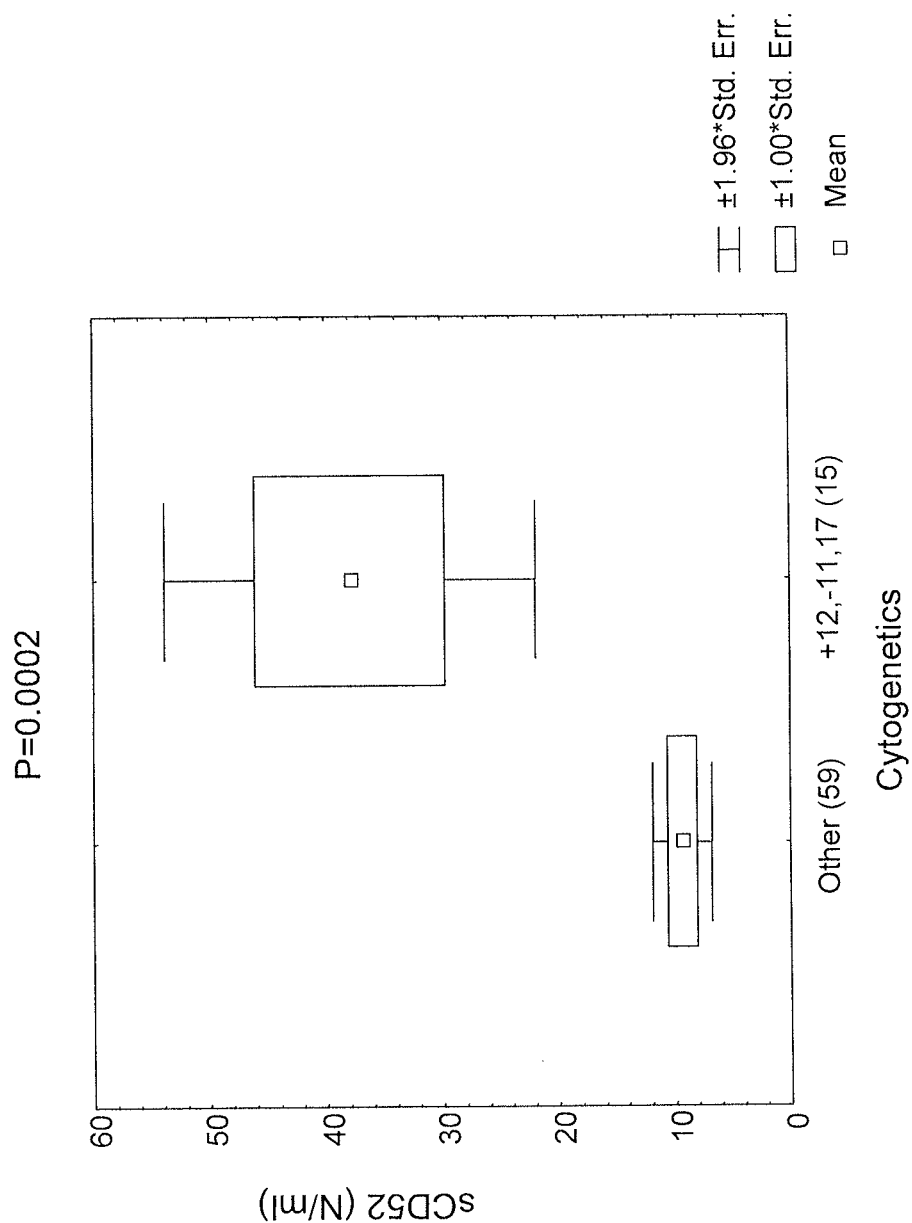
FIG. 12 illustrates that higher levels of sCD52 are detected in CLL patients with poor cytogenetics.
Figure 13:
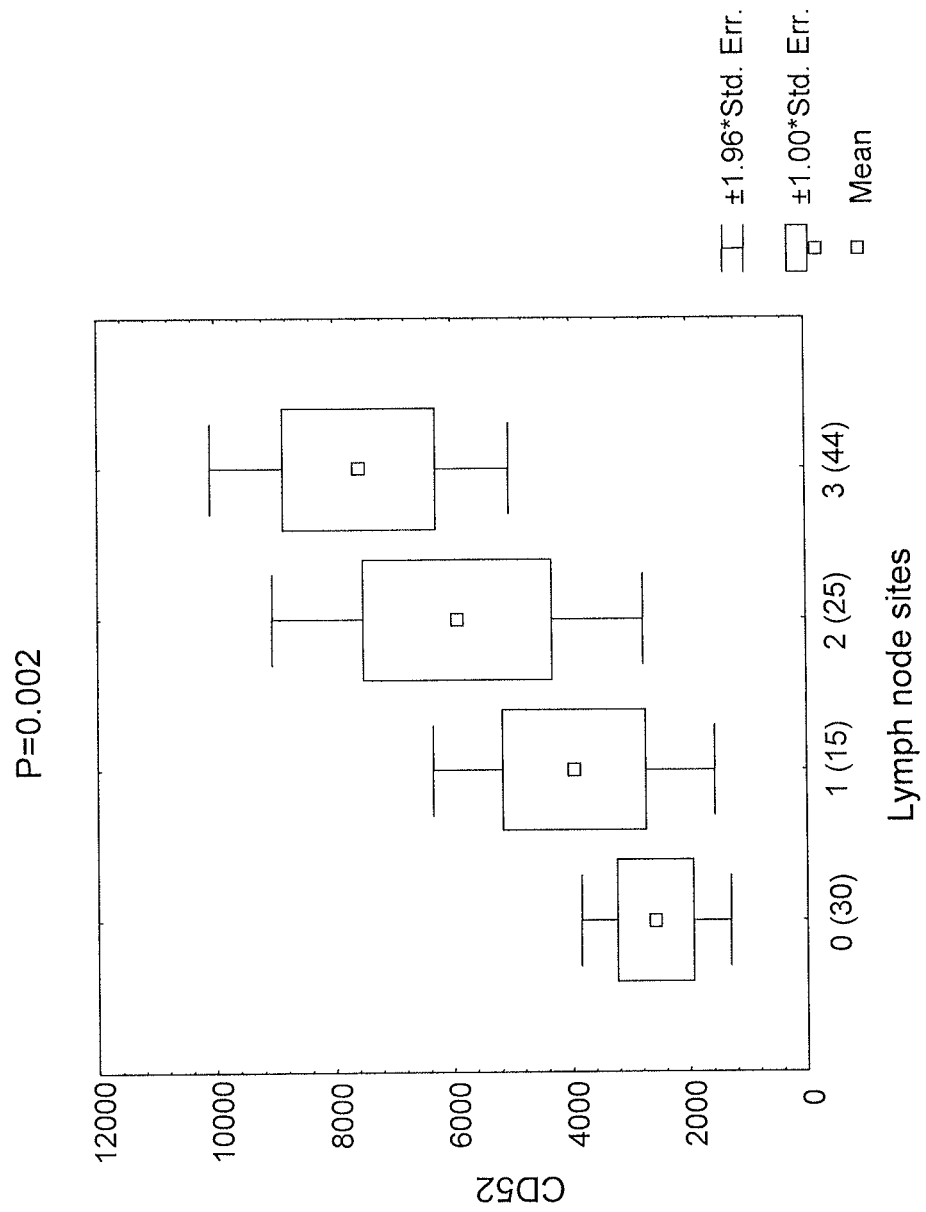
FIG. 13 illustrates that higher levels of sCD52 are detected in patients with higher number of lymph node sites with enlarged lymph nodes.

Clinical Relevance of Soluble CD52 in CLL Patients sCD52 levels were studied in 116 CLL patients. The characteristics of these patients are listed in Table 1. Of the 116 patients 66 (57%) were previously untreated. Seventy-nine (68%) were males and 44 (38%) were in stage III to IV of Rai stage. The median age of the patient was 61 and the median white-cell count was $60.1 \times 10^9/L$. Median hemoglobin was 12.7 g/l and the median β-microglobulin ($\beta_2M$) was 3.6 g/dL. Upon correlating the plasma levels of CD52 with Rai staging, there was significant correlation (p=0.0008, Kruskal-wallis) (FIG. 10). Also, there was a similar correlation when Binet Staging (p<0.0001)(FIG. 11) was used. Of the 116 patients, 74 had complete cytogenetic studies and sCD52 levels were compared between patients with poor cytogenetics (11q21−, +12, or abnormality on chromosome 17) and patients with other patients. Patients with poor cytogenetic had significantly higher levels of sCD52 (p=0.0002, kruskal-wallis) (FIG. 12). Plasma CD52 levels also correlated with the number of lymph node sites with enlarged lymph node. As shown in FIG. 13 higher levels of sCD52 were detected in the plasma of patients with higher number of lymph node sites with enlarged lymph nodes (P=0.002). sCD52 levels also positively correlated with increasing size of liver (P=0.0005) and spleen (0.000002) (Table 5). There was negative correlation between sCD52 levels and hemoglobin (P<0.00001) and platelets (P<0.00001) (Table 5). sCD52 levels directly correlated with total white cell count (WBC) (p<0.00001), $\beta_2M$ (P=0.00002), and surface expression of CD38 (0.01) (Table 5). Using Cox proportional hazard model and univariate analysis, sCD52 strongly correlated with survival. Higher levels of sCD52 correlated with shorter survival (p=0.001). Univariate analysis also showed that survival in this patient group correlated with Rai staging (p=0.007), surface CD38 expression (0.02), poor cytogenetics (p=0.005), hemoglobin (p=0.001), platelets (p=0.01), and $\beta_2M$ (0.00001). Thus, the data suggested that this group of patients was representative of CLL patients in general.

Figure 14:
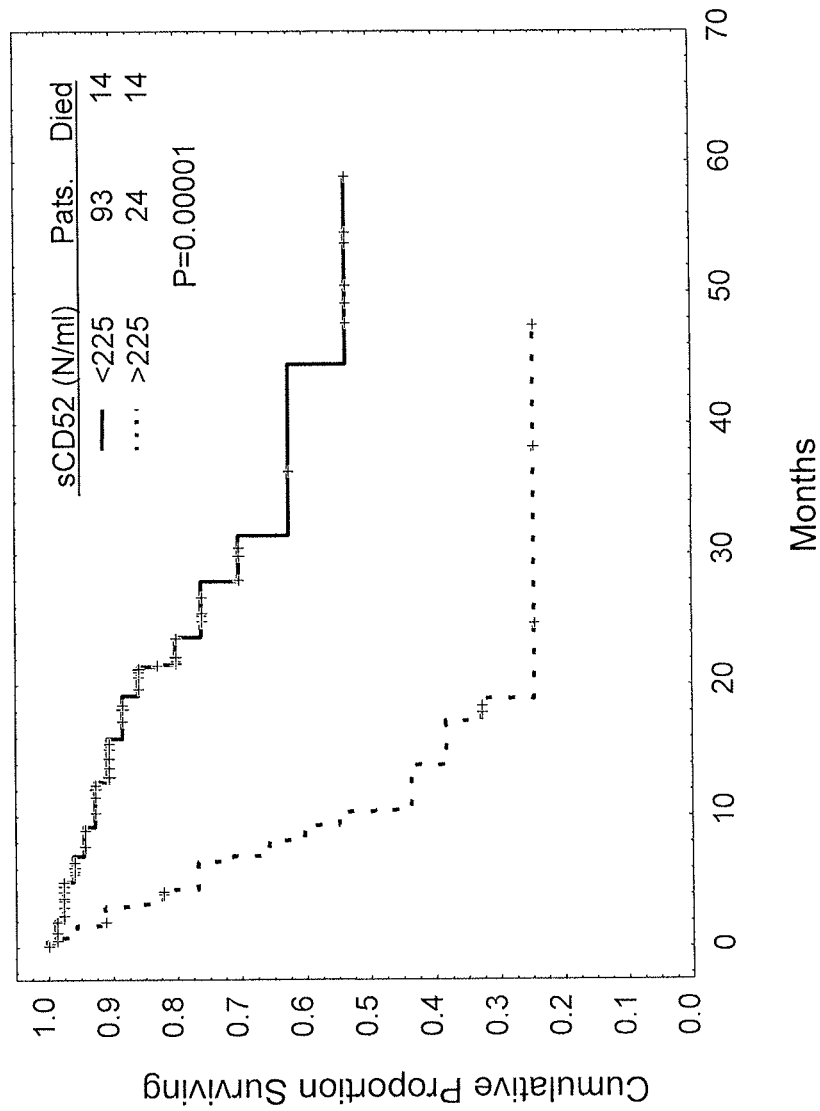
FIG. 14 illustrates that patients with high levels of sCD52 have a shorter survival than patients with low levels of sCD52.

In multivariate analysis incorporating sCD52, Rai staging, hemoglobin, platelets, WBC, and $\beta_2M$, only $\beta_2M$ was predictive of survival (p=0.02) while sCD52 was not predictive of survival. A cut-off point was used to separate the patients into two groups, one with high expression and one with low expression. Upon using a cut-off point of 32, which correspond to the upper quartile, patients with high levels of sCD52 showed significantly shorter survival (p=0.0001, Log-Rank test) (FIG. 14). Using sCD52 levels to separate CLL patients into two groups in a multivariate analysis incorporating Rai staging, hemoglobin, platelets, WBC, and $\beta_2M$, it was found that $\beta_2M$ remained a predictor of survival (p=0.05) and sCD52 was a borderline predictor of survival (P=0.06), while Rai, hemoglobin, platelets, and WBC were not predictors of survival. This suggested that sCD52 levels were possibly independent predictor of survival when they were at very high levels.

TABLE 4

Patients Characteristics.

| Characteristic | Patients (%) |
|---|---|
| Male | 79 (68) |
| Rai III-IV | 44 (38) |
| No prior Rx | 66 (37) |
| Splenomegaly | 43 (37) |
|  | Median (range) |
| Age | 61 (34-84) |
| WBC × $10^3$/ul | 60.4 (1.4-333) |
| HGB | 12.7 (4.0-17.8) |
| B2M mg/L | 3.6 (1.3-11.5) |

TABLE 5

Spearman correlation between sCD52 levels and various clinical characteristics in CLL.

|  | R | p-value |
|---|---|---|
| Hepatomegly (cm) | .31 | .0005 |
| Splenomegly (cm) | .43 | .000002 |
| HGB | −.45 | .000000 |
| PLT | −.39 | .000008 |
| WBC | .53 | .000000 |
| LYM | .21 | .01 |
| β2M | .41 | .00002 |
| CD38/CD19 | .44 | .01 |
| TNF-α | .38 | .0003 |
| AGE | .08 | .4 |

These data demonstrated that sCD52 levels reflected specific clinical behavior in CLL. sCD52 levels correlated with various stages of the disease and higher levels were associated with aggressiveness of the disease. There was a direct correlation between the number of leukemic cells in circulation, hepatomegaly, splenomegaly, lymph node involvement, and $\beta_2M$; all of which were usually associated with more advanced disease. Therefore, sCD52 can be used for staging patients, but more importantly the presence of sCD52 may have significant impact on the effectiveness of therapy of these patients when they are treated with Campath-1H. The possibility that sCD52 may bind to the therapeutic Campath-1H antibodies and sequester them from reaching the cells should be considered and investigated. This binding may have significant impact on the pharmakodynamics and pharmakokenetics of the antibodies. It is possible that patients with high levels of sCD52 require higher dosages of antibodies to saturate the sCD52 and allow the antibodies to reach cells. Similarly, it is possible that patients on therapy will require lower levels of antibodies as their sCD52 levels decrease and the tumor mass become smaller. Reducing dosages of anti-CD52 antibodies may help in reducing the severe immunsuppression reported in patients treated with Campath-1H. Using sCD52 may also be useful for monitoring the CLL disease and monitoring the effectiveness of therapy, irrespective if it is based on Campath-1H or not.

Example 11

Detection of sCD52/Campath-1H Complexes in Patients Treated with Campath-1H

The detection of sCD52 in the plasma of patients with CLL led the inventor to investigate the possibility that antigens and antibodies may form complexes in the plasma.

Figure 15:
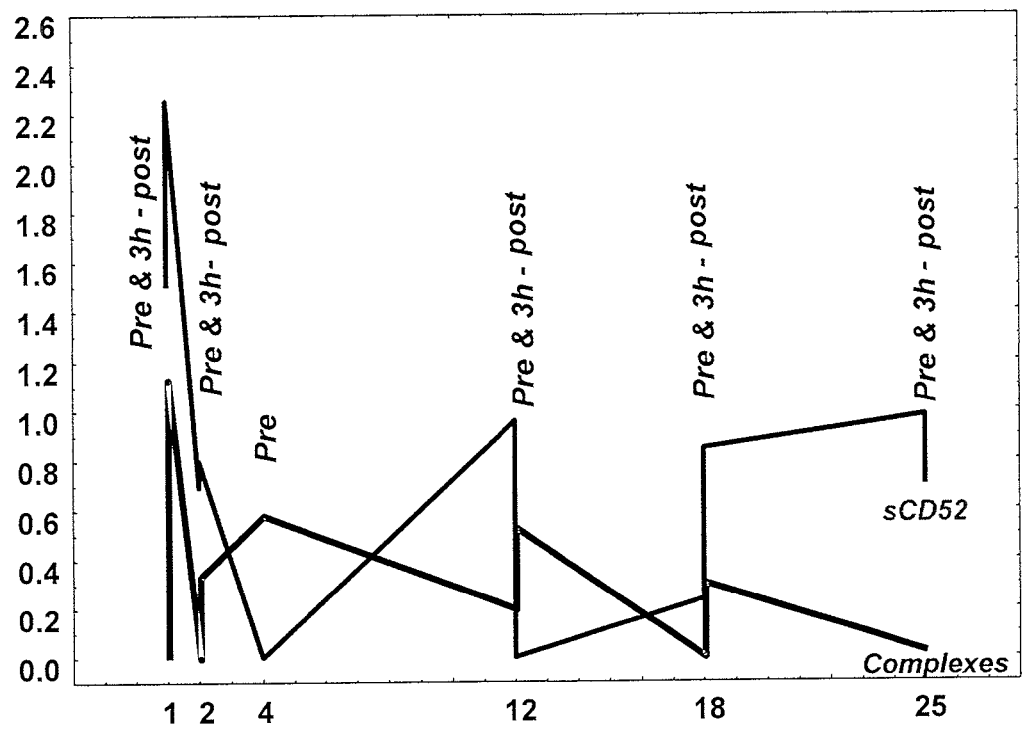
FIG. 15 shows the detection of the sCD52/Campath-1H complexes in a CLL patient being treated with Campath-1H for minimal residual. Levels of sCD52 are also shown.

Plasma sCD52/Campath-1H complexes were measured using a similar sandwich ELISA assay. Briefly, a ninety-six well polystyrene microplate was coated with capturing antibody for CD52 and washed as described above. Plasma samples were added after 1:100 dilution in PBS and incubated as described above. For detection, goat anti-human immunoglobulin that was horseradish peroxidase conjugated was used. The wells were then washed 6 times with PBS containing 0.01% Tween 20. 100 units of substrate were added for the development of the color and incubated for 15 to 30 minutes with constant shaking. The reaction was then stopped with 15 microliters of sodium chloride, the plates were read at 450 nm wavelength. Serial dilution of known number of molecules of synthetic CD52 peptide after binding at saturation to Campath-1H was used to generate a standard curve.

sCD52/Campath-1H immune complexes were detected in samples from CLL patients treated with Campath-1H. The ELISA assay showed linear correlation between dilutions of known amount of synthetic peptide mixed with excess Campath-1H (R=1). Immune complexes were detected in serial samples from a patient being treated with Campath-1H (FIG. 15).

The detection of sCD52/Campath-1H complexes in patients treated with Campath-1H suggests that the formation of these complexes were capable of reducing the amount of antibody available to attach to target cells.

Example 12

Correlation Between Campath-1H and Response to Therapy in CLL

Campath-1H levels were measured in patients with CLL treated with Campath-1H to eradicate minimal residual disease after chemotherapy. All patients were either in complete remission (CR), but had flow cytometry evidence of residual disease, or in partial remission (PR). The patients were treated with Campath-1H 10 mg three times a week for one month. The plasma levels of Campath-1H were correlated with residual disease as determined by polymerase chain reaction (PCR), response to therapy, and infection.

Briefly, plasma samples were collected from 12 patients at the end of the course. Some patients achieved complete remission (CR) and some patients had no response (NR). Patients with CR had significantly higher levels of Campath-1H as compared to NR patients (P=0.009). The median plasma Campath-1H level in patients achieving CR was 0.420 µg/ml (range 0-1.760 µg/ml), while all NR patients had no detectable plasma Campath-1H. Patients achieving CR had significantly lower minimal disease as detected by PCR (P=0.02). Patients who started on therapy with more residual disease as detected by PCR had less probability of achieving CR (P=0.02). Patients with evidence of infection (3 with CMV and one with *Staphylococcus*) had significantly more residual disease (P=0.02) as determined by PCR, but these patients had no statistically significant difference in Campath-1H levels compared to those who did not develop infection.

Thus, this data suggested that CLL patients with higher levels of residual disease may require higher doses of Campath-1H to eradicate disease and detectable plasma levels of Campath-1H may be necessary for achieving CR. Furthermore infection in this group of patients was associated with higher levels of residual disease and not higher levels of Campath-1H.

Example 13

Correlation Between Rituximab Levels and Response in Patients with CLL Treated with Fludarbine, Cyclophosphamide and Rituximab Combination Treating CLL patients with fludarbine (F), cyclophosphamide (C) and Rituximab (R) combination (Six cycles of FCR (F-25 mg/m2/day and C-250 mg/m2/day on days 2-4 of cycle 1 and on days 1-3 of cycles 2-6 and R-375 mg/m2 on day 1 of cycle 1 and R-500 mg/m2 on day 1 of cycles 2-6) has resulted in success, such as achieving remission (CR).

Briefly, plasma Rituximab levels were measured in patients with CLL treated with FCR at various time between 3 and 9 months of initiating therapy and the levels were correlated with response and other characteristics. When front-line patients were considered, patients who had no response, had no detectable levels of Rituximab. These patients had significantly higher levels of circulating CD20 (cCD20) as compared with patients with CR or nodular CR (CRN). However, when previously treated patients were considered, Rituximab levels were not significantly different between patients in CR, NR, and CRN. Higher Rituximab levels were achieved in patients who were in earlier Rai stage at the time of initiating therapy (P=0.005) in front-line patients, but not in previously treated patients (P=0.7). The achieved Rituximab levels correlated negatively with before therapy $\beta_2 M$ (R=−0.44, P=0.002) in previously treated patients, but not in front-line patients (R=0.20, P=0.23).

Thus, this data suggested that the few front-line patients treated on FCR, who did not respond to therapy, had low levels of Rituximab and may benefit from higher doses.

REFERENCES CITED

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,472,509
U.S. Pat. No. 4,938,948
U.S. Pat. No. 5,021,236
U.S. Pat. No. 5,196,066
U.S. Pat. No. 5,739,169

U.S. Pat. No. 5,801,005
U.S. Pat. No. 5,824,311
U.S. Pat. No. 5,830,880
U.S. Pat. No. 5,846,945
Algino et al., Am J Clin Pathol. 1996; 106:78-81
Almasri et al., Am J Hematol. 1992; 40:259-263
Atherton et al., Biol. of Reproduction, 32, 155-171, 1985.
Austin-Ward and Villaseca, Rev. Med. Chil., 126:838-45, 1998.
Bajorin et al., Proc. Annu. Meet. Am. Soc. Clin. Oncol., 7:A967, 1988.
Becker et al., The new S language. Pacific Grove, Calif., Wadsworth, 1988
Belov, L. et al., Cancer Res 61:4483, 2001
Berberian et al., Science, 261:1588-1591, 1993.
Bindon, C. I. et al., Eur J Immunol 18:1507, 1988
Breiman et al., Classification and regression trees. Pacific Grove, Calif., Wadsworth, 1984
Brodeur et al., Monoclonal Antibody Production Techniques and Applications, Marcel Dekker, Inc., New York, 1987)
Bukowski et al., Clin. Cancer Res., 4(10):2337-47, 1998.
Christodoulides et al., Microbiology, 144(Pt 11):3027-37, 1998.
Cleary et al., Trends Microbiol., 4:131-136, 1994.
Cleveland, J. American Statistical Association. 1979; 74:829-836
Cox D R., J. R. Statistical Soc. 1972; 34:187-220
Davidson et al., J. Immunother., 21:389-98, 1998.
De Jager R, et al., Semin Nucl Med 23(2):165-179, 1993.
Deans et al., J Biol Chem. 1995; 270:22632-22638
Deans et al., J Biol Chem. 1998; 273:344-348
Dholakia et al., J. Biol. Chem., 264, 20638-20642, 1989.
Dick, A. D. et al., Br J Ophthalmol 84:107, 2000
Dillman, Cancer Biother. Radiopharm., 14(1):5-10, 1999.
Dimopoulous et al., J Clin Oncol. 2000; 18:214-226
Doolittle M H et al., Methods Mol Biol., 109:215-237, 1999.
Dybjer, A. et al., Leuk Lymphoma 37:437, 2000
Dyer, M. J. et al., Semin Oncol 26:52, 1999
Elsner, J. et al., Blood 88:4684, 1996
Finkelstein, J. B. J Natl Cancer Inst 93:175, 2001
Flynn and Byrd J C, Curr Opin Oncol. 2000; 12:574-581
Friend, P. J., et al., Transplant Proc 23:2253, 1991
Galiegue-Zouitina et al., Genes Chromosomes Cancer. 1994; 11:246-255
Gilleece, M. H. et al., Blood 82:807, 1993
Ginaldi et al., J Clin Pathol. 1998; 51:364-369
Ginaldi, L. et al., Leuk Res 22:185, 1998
Goding, In: Monoclonal Antibodies: Principles and Practice, pp. 60-61, and 71-74, 1986.
Golay et al., J Immunol. 1985; 135:3795-3801
Greenwood, J. et al., Ther Immunol 1:247, 1994
Gulbis B et al., Hum Pathol 24(12):1271-1285, 1993.
Hainsworth, Semin Oncol. 2000; 27:25-29
Hale et al., Bone Marrow Transplant. 2000; 26:69-76
Hale, C. et al., Immunology 88:183, 1996
Hale, G. et al., Bone Marrow Transplant 26:69, 2000
Hale, G. et al., Br J Haematol 60:41, 1985
Hale, G. et al., Tissue Antigens 35:118, 1990
Hanibuchi et al., Int. J. Cancer, 78:480-5, 1998.
Hellstrand et al., Acta. Oncol., 37:347-53, 1998.
Hofmeister et al., Blood Cells Mol Dis. 2000; 26:133-143
Hui and Hashimoto, Infect. Immun., 66:5329-36, 1998.
Ibrahim, S. et al., Blood 98:181, 2001
Irie & Morton, Proc. Nat'l Acad. Sci. USA 83:8694-8698, 1986
Irie et al., Human Tumor Antigens and Specific Tumor Therapy, Metzgar & Mitchell (eds.), Alan R. Liss, Inc., New York, pp. 115-126, 1989.
Isaacs, J. D. et al., Lancet 340:748, 1992
Jakobovits et al., Nature 262:255-258, 1993.
Jakobovits et al., Proc. Natl. Acad. Sci. USA 90:2551-2555, 1993.
Jones et al., Nature 321:522-525, 1986.
Kalil, N. et al., Drugs Aging 16:9, 2000
Kang et al., Science, 240:1034-1036, 1988.
Kaplan et al., J. American Statistical Association. 53:457-481
Keating and O'Brien, Semin Oncol. 2000; 27:86-90
Keating, M. J. Semin Oncol 26:107, 1999
Kehrl et al., Immunol Today. 1994; 15:432-436
Khatoon et al., Ann. of Neurology, 26, 210-219, 1989.
Khorana et al., Leuk Lymphoma. 2001; 41:77-87
Khorana, A. et al., Leuk Lymphoma 41:77, 2001
King et al., J. Biol. Chem., 269, 10210-10218, 1989.
Kirchhoff, C et al., Cells Tissues Organs 168:93, 2001
Kirchhoff, C. et al., Adv Exp Med Biol 424:221, 1997
Kirchhoff, C. et al., Andrologia 30:225, 1998
Kirchhoff, C. et al., Mol Hum Reprod 2:9, 1996
Kirchhoff, C. et al., Mol Reprod Dev 34:8, 1993
Kirchhoff, C. et al., Mol Reprod Dev 56:26, 2000
Kirchhoff, C. et al., Rev Reprod 3:86, 1998
Kohler et al., Methods Enzymol., 178:3, 1989.
Kohler and Milstein, Eur. J. Immunol., 6:511-519, 1976
Kozbor J. Immunol. 133:3001, 1984.
Kreier et al., Infection, Resistance and Immunity, Harper & Row, New York, (1991)).
Kuehnle et al., Blood. 2000; 95:1502-1505
Lenert et al., Science, 248:1639-1643, 1990.
Lim, S. H. et al., Br J Haematol 84:542, 1993
Lim, S. H. et al., Lancet 341:432, 1993
Lockwood, C. M. Adv Exp Med Biol 336:235, 1993
Lockwood, C. M. et al., Lancet 341:1620, 1993
Lockwood, C. M. et al., Qjm 89:903, 1996
Maloney D G. Semin Oncol. 1999; 26:74-78
Mantel, Cancer Chemotherapy Reports. 1966; 60:163-170
Marti et al., Ann N Y Acad Sci. 1992; 651:480-483
Matteson, E. L. et al., Arthritis Rheum 38:1187, 1995
Matutes, E. Cancer Control 5:19, 1998
McCafferty et al., Nature 348:552-553, 1990
McLaughlin et al., Semin Oncol. 2000; 27:37-41
Mehta, J. et al., Leuk Lymphoma 25:479, 1997
Mitchell et al., Ann. N.Y. Acad. Sci., 690:153-166, 1993.
Mitchell et al., J. Clin. Oncol., 8:856-859, 1990.
Moreau, T. et al., Mult Scler 1:357, 1996
Morton D. L., and Ravindranath, M. H. Current concepts concerning melanoma vaccines. In Tumor Immunology, Dalgleish A G (ed.), London: Cambridge University Press, 1-55, 1996.
Morton et al., Ann. Surg. 216: 463-482, 1992.
Naparstek, E. et al., Br J Haematol 89:506, 1995
Naparstek, E. et al., Exp Hematol 27:1210, 1999
Novitzky, N. et al., Transplantation 67:620, 1999
Or, R. et al., Bone Marrow Transplant 13:97, 1994
O'Shannessy et al., J. Immun. Meth., 99, 153-161, 1987.
Owens & Haley, J. Biol. Chem., 259:14843-14848, 1987.
Pawson, R. et al., J Clin Oncol 15:2667, 1997
Pietras et al., Oncogene, 17:2235-49, 1998.
Popoff et al., Mol Immunol. 1998; 35:207-214
Potter & Haley, Meth. in Enzymol., 91, 613-633, 1983.
Poynton, C. H. et al., Lancet 341:1037., 1993
Qin et al., Proc. Nat'l Acad. Sci. USA, 95(24):1411-6, 1998.
Ravindranath, M. H. and Morton, D. L. Intern. Rev. Immunol. 7: 303-329, 1991.

Rawstron, A. C. et al., Blood 98:29, 2001
Riechmann et al., Nature 332:323-327, 1988.
Riechmann, L. et al., Nature 332:323, 1988
Riley and Sliwkowski M X, Semin Oncol. 2000; 27:17-24
Rooney, I. A. et al., J Clin Invest 97:1675, 1996
Rosenberg et al., Ann. Surg., 210:474, 1989.
Rosenberg et al., N. Engl. J. Med., 319:1676, 1988
Rowan, W et al., Immunology 95:427, 1998
Salisbury, J. R. et al., J Clin Pathol 47:313, 1994
Sasso et al., J. Immunol., 142:2778-2783, 1989.
Shorki et al., J. Immunol., 146:936-940, 1991.
Silvermann et al., J. Clin. Invest., 96:417-426, 1995.
Slamon et al., N Engl J Med. 2001; 344:783-792
Steinberg D, Colla P: CART: Tree-structured non-parametric data analysis. San Diego, Calif., Salford Systems, 1995
Streckfus et al., Clin Cancer Res. 2000; 6:2363-2370
Taylor M L et al., Clin Immunol 94:33, 2000
Tedder and Engel, Immunol Today. 1994; 15:450-454
Tedder and Schlossman J Biol Chem. 1988; 263:10009-10015
Tone, M. et al., Biochim Biophys Acta 1446:334, 1999
Treumann A, et al., J Biol Chem 270:6088, 1995
van Der Velden V H et al., Blood. 2001; 97:3197-3204
Verhoeyen et al., Science 239:1534-1536, 1988.
Verstovsek, S. et al., Leukemia 15:1165, 2001
Warzynski et al., Cytometry. 1994; 18:88-92
Wing, M. G. et al., Ther Immunol 2:183, 1995
Wing, M. G. et al., J Clin Invest 98:2819, 1996
Xia, M. Q. et al., Mol Immunol 30:1089, 1993
Xia, M. Q. et al., Biochem J 293:633, 1993
Xia, M. Q. et al., Eur J Immunol 21:1677, 1991
Yeung, C. H. et al., Mol Hum Reprod 7:617, 2001
Yeung, C. H. et al., Mol Hum Reprod 3:1045, 1997
Zinzani et al., J Clin Oncol. 2000; 18:3875-3877

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of monitoring the progress of therapy in patient being treated with a therapeutic anti-CD33 antibody, the method comprising testing a sample from the patient to measure the level of circulating cell-free CD33, circulating cell-free anti-CD33 or circulating cell-free CD33/anti-CD33 complexes.

2. The method of claim 1, wherein the sample is selected from the group consisting of serum, cell lysate and plasma.

3. The method of claim 1, wherein the patient is being treated with Mylotarg.

4. The method of claim 1, wherein the sample is tested to measure the level of circulating cell-free CD33.

5. The method of claim 1, wherein the sample is tested to measure the level of circulating cell-free anti-CD33.

6. The method of claim 1, wherein the sample is tested to measure the level of circulating cell-free CD33/anti-CD33 complexes.

* * * * *